(12) United States Patent
Weiss et al.

(10) Patent No.: US 10,221,283 B2
(45) Date of Patent: Mar. 5, 2019

(54) AMINO-SUBSTITUTED POLYSILOXANES COMBINED WITH POLYMERIZABLE AND UNPOLYMERIZABLE ORGANIC ACIDS

(71) Applicant: Georgetown University, Washington, DC (US)

(72) Inventors: Richard G. Weiss, Bethesda, MD (US); Ajaya M. V. Mallya, Washington, DC (US); Yong He, Arlington, VA (US); Tao Yu, Arlington, VA (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 14/761,680

(22) PCT Filed: Jan. 17, 2014

(86) PCT No.: PCT/US2014/012000
§ 371 (c)(1),
(2) Date: Jul. 17, 2015

(87) PCT Pub. No.: WO2014/113643
PCT Pub. Date: Jul. 24, 2014

(65) Prior Publication Data
US 2015/0361224 A1 Dec. 17, 2015

Related U.S. Application Data

(60) Provisional application No. 61/904,549, filed on Nov. 15, 2013, provisional application No. 61/754,274, filed on Jan. 18, 2013.

(51) Int. Cl.
*C08G 77/38* (2006.01)
*C08G 77/388* (2006.01)
*A61K 47/34* (2017.01)
*C08G 77/392* (2006.01)
*H01M 4/60* (2006.01)

(52) U.S. Cl.
CPC ............. *C08G 77/38* (2013.01); *A61K 47/34* (2013.01); *C08G 77/388* (2013.01); *C08G 77/392* (2013.01); *H01M 4/602* (2013.01)

(58) Field of Classification Search
CPC ........ C08G 77/26; C08G 77/38; C08G 77/80; C08L 83/08; C09J 183/08
See application file for complete search history.

(56) References Cited

U.S. PATENT DOCUMENTS

| 5,567,428 | A | 10/1996 | Hughes | |
|---|---|---|---|---|
| 5,620,796 | A * | 4/1997 | Kawabata | C08F 220/18 428/355 AC |
| 6,124,490 | A * | 9/2000 | Gormley | A61K 8/0208 106/287.11 |
| 2004/0001799 | A1 * | 1/2004 | Lu | A61K 8/898 424/70.122 |
| 2006/0142434 | A1 | 6/2006 | Weerawarna | |
| 2011/0091511 | A1 * | 4/2011 | Nguyen | A61K 9/7061 424/400 |
| 2011/0104085 | A1 * | 5/2011 | Klug | A61K 8/898 424/59 |
| 2013/0172419 | A1 * | 7/2013 | Saxena | C08G 77/38 514/570 |

FOREIGN PATENT DOCUMENTS

| JP | 2003185862 A | * | 7/2003 | |
| JP | WO 2011119218 A1 | * | 9/2011 | ............. C08G 77/26 |
| WO | WO-2011/119218 A1 | | 9/2011 | |

OTHER PUBLICATIONS

Tamaki et al (JP 2003185862 A, English translation from Espacenet, downloaded Jun. 2017).*
Dow Answer Center (What are the storage considerations for acrylic acid?, https://dowac.custhelp.com/app/answers/detail/a_id/2465, Updated Mar. 26, 2018) (Year: 2018).*
Angell, C. A. et al., "Fuel cell using the protic ionic liquid and rotator phase solid electrolyte principles". *Defense Technical Information Center*, Mar. 8, 2010.
O'Brien, K. W., "Synthesis of Functionalized Poly(dimethylsiloxane)s and the Preparation of Magnetite Nanoparticle Complexes and Dispersions", Virginia Polytechnic Institute and State University, 2003.

* cited by examiner

*Primary Examiner* — Mark V Stevens
(74) *Attorney, Agent, or Firm* — Lathrop Gage LLP; Alan W. Steele

(57) ABSTRACT

Provided is a composition comprising (i) a polysiloxane comprising a plurality of pendant amines and (ii) an acid. Also provided is a composition comprising (i) a polysiloxane comprising a plurality of pendant acids and (ii) an amine. The compositions are useful inter alia for chemical or oil spill cleanup, drug delivery systems, transparent films, adhesives, binding agents, conductors, membranes, cross-linking agents, or opticoelectronic applications. Also provided are methods for making the compositions of the invention, as well as a battery and a composition for controlled release of a compound, each comprising a composition of the invention.

7 Claims, 28 Drawing Sheets

AMINO-SUBSTITUTED POLYSILOXANES COMBINED WITH POLYMERIZABLE AND UNPOLYMERIZABLE ORGANIC ACIDS

RELATED APPLICATIONS

This application is the U.S. national phase of International Patent Application No. PCT/US2014/012000, filed Jan. 17, 2014, which claims the benefit of priority to U.S. Provisional Patent Applications Ser. No. 61/754,274, filed Jan. 18, 2013; and 61/904,549, filed Nov. 15, 2013.

BACKGROUND

Polysiloxanes have a myriad of uses in daily life, and many substituted polysiloxanes have allowed the list of uses to become even larger. Amino groups attached to the side chains of polysiloxane backbones offer an attractive platform from which subtle chemical changes can be made easily, leading to large changes in the bulk properties of the materials. Simple alterations of amino-substituted polysiloxanes have been exploited to produce new materials. For example, addition of an uncharged triatomic molecule, such as $CO_2$ or $CS_2$, can create ionic centers within the polymer matrixes that have a profound effect on the viscosity, adhesive, and swelling properties of a polysiloxane. Depending on the nature of the triatomic molecule added, the post-addition treatment, the percent of monomers in the polysiloxane with an amino functionality, and the type of amino group, the materials can be transformed from the free-flowing, slippery liquids to strong (reversible) adhesives and very viscous syrups, rubbery materials, or gels, some of which are able to imbibe selectively large amounts of low polarity solvents.

The effects of other simple additives which are capable of creating ion pairs within the polysiloxanes on the polymer properties remain a potential source of cost-effective and useful materials.

SUMMARY OF THE INVENTION

An aspect of the present invention relates to polysiloxane materials containing a basic functional group (e.g., amine or other group capable of accepting a proton) combined with an acid to form materials with useful properties (e.g., as transparent films, adhesives, binding agents, conductors, membranes, or controlled-release systems). In certain embodiments, the acid is a mono-acid (e.g., acetic acid). In certain embodiments, the acid is a di-acid (e.g., succinic acid). In certain embodiments, the acid is a tri-acid. In certain embodiments, the acid contains an aromatic group.

An aspect of the present invention relates to polysiloxane materials containing an acidic functional group (e.g., carboxylic acid or other group capable of donating a proton) combined with a base to form materials with useful properties (e.g., as transparent films, adhesives, binding agents, conductors, membranes, or controlled-release systems). In certain embodiments, the base is mono-basic (e.g., butyl amine, di(isopropyl)amine, or triethylamine). In certain embodiments, the base is di-basic (e.g., ethylene diamine). In certain embodiments, the base is tri-basic. In certain embodiments, the base contains an aromatic group (e.g., aniline).

The changes in rheological, adhesive, and swelling properties that occur when a series of mono-carboxylic acids or di-carboxylic acids are added to 6-7PSil, a polysiloxane in which 6-7% of the side groups contain a primary amine functionality, give rise to materials useful as polymer networks for chemical or oil spill cleanup, drug delivery systems, transparent films, adhesives, binding agents, conductors, membranes, cross-linking agents, or opticoelectronic applications. Those changes are correlated with (especially) the structures of the acids. In addition, described herein are materials made from in situ photo-polymerization of unsaturated carboxylic acids that were added to the polysiloxane. The results demonstrate that drastic changes effected by such additions (or polymerizations) lead to materials with drastically different properties than those of the parent polysiloxane. Clearly, the materials may be useful in a variety of new applications, and the protocols described here can be applied directly to other amino-substituted polymers, including those which are not polysiloxanes.

Polysiloxane ammonium salts have wide-ranging utility primarily based on the unique character of silicon-containing polymers (e.g., stability, low water solubility) and their adaptability to various technical fields. Polysiloxanes exhibit low surface tension, high flexibility, excellent stability to heating, and resistance to oxidation and aging. However, the high malleability and relatively low viscosity of polysiloxane can be disadvantageous because they can't be made into fibers and immobilized films without significant structural modifications, such as crosslinking Crosslinking systems have been designed consisting of the polysiloxane amine and $CO_2$ or $CS_2$. At the same time, it is widely known that amines form ammonium salts when combined with an acid. So polysiloxane ammonium salt could be easily produced with polysiloxane amine, but it would exhibit higher hydrophilicity than polysiloxane amine, which may lead to different aggregation, solubility, rheology or swelling properties.

In the present invention, ammoniumpolysiloxane networks with acids such as carboxylates are produced from aminopolysiloxane such as 6-7PSil or $D_2EDA$ (see structure in Scheme 1) and different mono-acids or di-acids. Ionic crosslinking could be realized through the salt formation reaction of the two carboxylic groups of a diacid compound, or even through electrostatic interactions when a monocarboxylic acid was employed.

DETAILED DESCRIPTION

Figure 1:
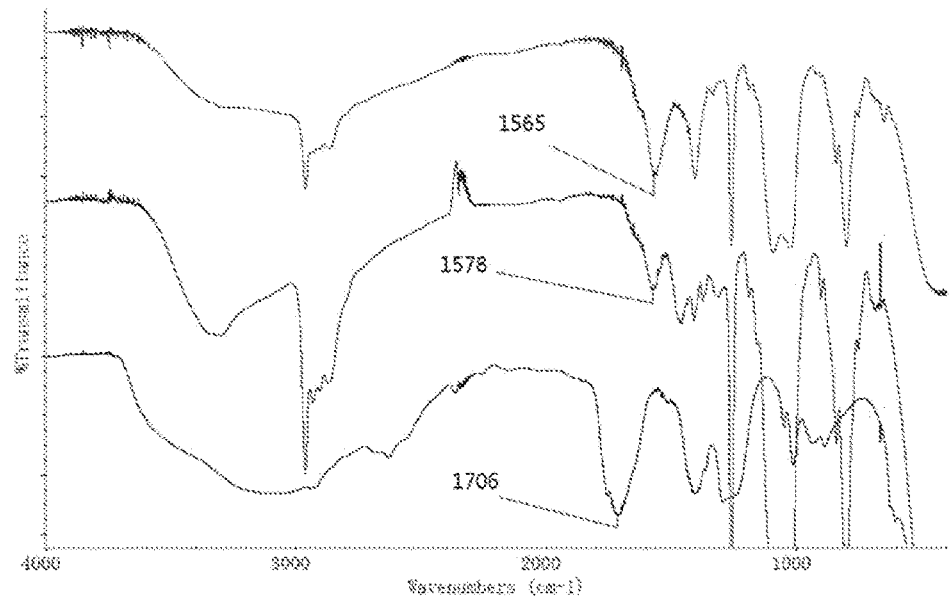
FIG. 1 depicts vertically offset IR spectra of acetic acid (bottom), $D_2EDA$ (middle), and ammonium acetate of $D_2EDA$ (top, with one equivalent of acetic acid), synthesized as described for 6-7PSil.

Aminoalkylfunctional silicones have a broad array of applications as a result of their chemical reactivity, their ability to form hydrogen bonds and, particularly in the case of diamines, their chelating ability. Additional reactivity can be built into aminoalkyl groups in the form of alkoxy groups. Aminoalkylsiloxanes are available in the three classes of structures typical for silicone polymers: terminated, pendant group and T-structure. Aminopropyl terminated polydimethylsiloxanes react to form a variety of polymers including polyimides, polyureas and polyurethanes. Block polymers based on these materials are becoming increasingly important in microelectronic (passivation layer) and electrical (low-smoke generation insulation) applications. They are also employed in specialty lubricant and surfactant applications. They may also be used in antifouling coatings (e.g., as bactericidal coatings), particularly when the polymer contains quaternary amines.

An aspect of the invention is a composition, comprising a polysiloxane comprising a plurality of pendant amines; and an acid selected from the group consisting of carboxylic acids, sulfonic acids, HCl, HBr, HI, HNO$_3$, H$_2$SO$_4$, H$_3$PO$_4$, B(OH)$_3$, HClO$_3$, and HClO$_4$. In one embodiment, each of the plurality of pendant amines is attached to the polysiloxane via an alkyl chain optionally substituted with one or more alkyl, haloalkyl, halide, aryl, or aralkyl groups.

In one embodiment, the acid is a carboxylic acid.

In one embodiment, the acid is a dicarboxylic acid.

In one embodiment, the acid is a carboxylic acid selected from the group consisting of acetic acid, ethanoic acid, propionic acid, pentanoic acid, hexanoic acid, trifluoroacetic acid, chloroacetic acid, dichloroacetic acid, trichloroacetic acid, methoxyacetic acid, acrylic acid, methacrylic acid, benzoic acid, vinylbenzoic acid, oxalic acid, malonic acid, succinic acid, glutaric acid, adipic acid, azelaic acid, terephthalic acid, phthalic acid, a perylene dicarboxylic acid, a nitrobenzoic acid, and a polymer comprising carboxylic acids.

In one embodiment, the acid is a sulfonic acid.

In one embodiment, the acid is methanesulfonic acid, trifluoromethanesulfonic acid, benzenesulfonic acid, p-toluenesulfonic acid, taurine, and a sulfonic-acid containing polymer.

In accordance with any one of the foregoing embodiments, in one embodiment the pendant amines are primary amines.

In accordance with any one of the foregoing embodiments, in one embodiment pendant amines are secondary amines.

In accordance with any one of the foregoing embodiments, in one embodiment the pendant amines are tertiary amines.

In accordance with any one of the foregoing embodiments, in one embodiment the pendant amines are quaternary amines.

In accordance with any one of the foregoing embodiments, in one embodiment the pendant amines are diamines or amidines.

In accordance with any one of the foregoing embodiments, in one embodiment the pendant amines are amidines.

In accordance with any one of the foregoing embodiments, in one embodiment the pendant amines are substituted with one, two, or three alkyl, alkenyl, alkynyl, cycloalkyl, aromatic, or alkoxy groups.

In accordance with any one of the foregoing embodiments, in one embodiment the pendant amines are acyclic.

An aspect of the invention is a composition, comprising a polysiloxane comprising a plurality of pendant acids selected from the group consisting of carboxylic acids and sulfonic acids; and an amine.

In one embodiment, each of the plurality of pendant acids is a carboxylic acid.

In one embodiment, each of the plurality of pendant acids is a carboxylic acid attached to the polysiloxane via an alkyl chain optionally substituted with one or more alkyl, haloalkyl, halide, aryl, or aralkyl groups.

In one embodiment, each of the plurality of pendant acids is a sulfonic acid.

In one embodiment, each of the plurality of pendant acids is a sulfonic acid attached to the polysiloxane via an alkyl chain optionally substituted with one or more alkyl, haloalkyl, halide, aryl, or aralkyl groups.

In accordance with any one of the foregoing embodiments, in one embodiment the amine is a primary amine.

In accordance with any one of the foregoing embodiments, in one embodiment the amine is a secondary amine.

In accordance with any one of the foregoing embodiments, in one embodiment the amine is a tertiary amine.

In accordance with any one of the foregoing embodiments, in one embodiment the amine is a quaternary amine.

In accordance with any one of the foregoing embodiments, in one embodiment the amine is a diamine or amidine.

In accordance with any one of the foregoing embodiments, in one embodiment the amine is an amidine.

In accordance with any one of the foregoing embodiments, in one embodiment the amine is substituted with one, two, or three alkyl, alkenyl, alkynyl, cycloalkyl, aromatic, or alkoxy groups.

In accordance with any one of the foregoing embodiments, in one embodiment the amine is acyclic.

Preferred embodiments of amino functionality pendant from the siloxane backbone include: (aminopropyl)-methylsiloxane-dimethylsiloxane copolymers and (aminoethyl-aminopropyl)-methylsiloxane-dimethylsiloxane copolymers. They are frequently used in modification of polymers such as epoxies and urethanes, internal mold releases for nylons and as lubricants, release agents and components in coatings for textiles and polishes. Aminoalkyl T-structure silicones are primarily used as surface treatments for textiles and finished metal polishes (e.g., automotive car polishes). The resistance to wash-off of these silicones is frequently enhanced by the incorporation of alkoxy groups which slowly hydrolyze and form crosslink or reactive sites under the influence of the amine. The same systems can be reacted with perfluorocarboxylic acids to form low surface energy (<7 dynes/cm) films.

The amino-functionalized or acid-functionalized polysiloxane scaffolds may be random or block copolymers. Non-limiting examples of amino-functionalized polysiloxane scaffolds include the following:

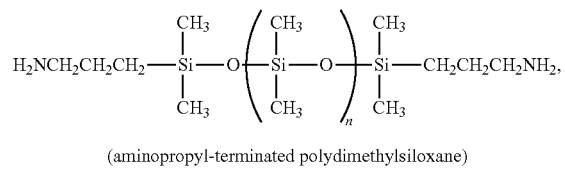

(aminopropyl-terminated polydimethylsiloxane)

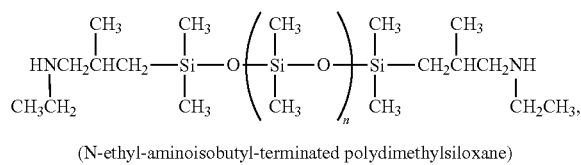

(N-ethyl-aminoisobutyl-terminated polydimethylsiloxane)

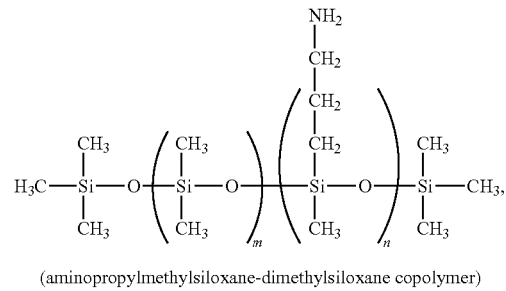

(aminopropylmethylsiloxane-dimethylsiloxane copolymer)

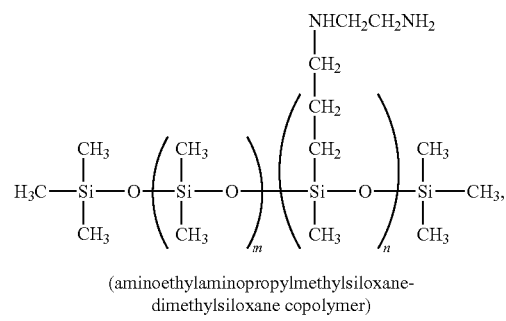

(aminoethylaminopropylmethylsiloxane-dimethylsiloxane copolymer)

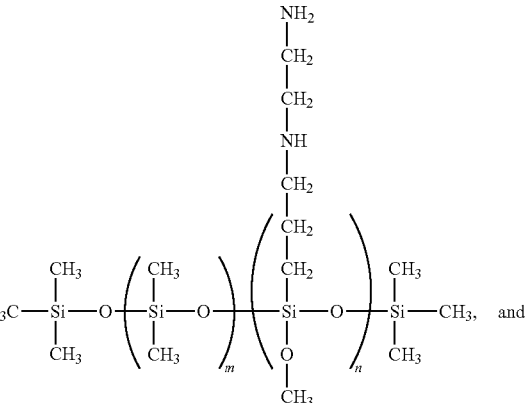

(aminoethylaminopropylmethoxysiloxane-dimethylsiloxane copolymer)

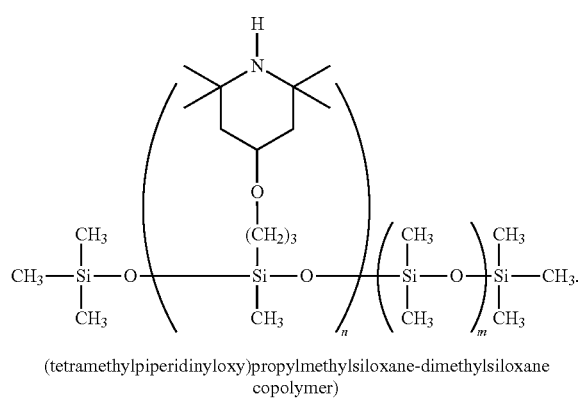

(tetramethylpiperidinyloxy)propylmethylsiloxane-dimethylsiloxane copolymer)

Replacement of any of the amine groups above with an acidic moiety such as —COOH, —CH$_2$COOH, SO$_3$H, or CH$_2$SO$_3$H, would yield the reversed polymer discussed in greater detail below.

The backbone may be modified so that the polymers are based on alternate polysiloxanes such as diethylsiloxane, diisopropylsiloxane, diphenylsiloxane, alkoxysiloxanes such as dimethoxysiloxane or diethoxysiloxane, haloalkylsiloxanes (e.g., fluoroalkylsiloxanes), or other polysiloxanes known in the art.

The mol % of amine functional groups in the polymer may vary substantially and may be selected to modulate one or more of the physical properties of the polymer to achieve a desired result. For example, a more viscous polymer may be obtained by an increase in the mol % of amine functional groups, leading to more protonation and thus more ionic interactions per unit of polymer weight. In certain embodiments, the mol % of the amine functional groups is about 0.05-0.1%, 0.1-1.0%, or 0.5-1%. In certain embodiments, the mol % of the amine functional groups is about 0.05-25%, 0.1-20%, 0.2-15%, 1-12%, 2-10%, 3-8%, 4-7%, 5-6%, 0.05-2%, 0.08-1%, or 1-2%.

Selection of a particular average molecular weight of the polysiloxane polymer will be determined by task at hand. For example, polymers with higher molecular weights tend to have higher viscosity, making them more useful in certain applications. In certain embodiments, the molecular weight is about 700-10,000, 800-9,000, 900-8,000, 1,000-7,000, 2,000-7,000, 3,000-6,000, or 4,000-5,000. Any range of molecular weights may be combined with any mol % of amine functional group recited above.

The identity of the amine functionality can greatly impact the properties of the polysiloxane polymer. Generally speaking, the amine may be substituted with one to three alkyl, alkenyl, alkynyl, cycloalkyl, aromatic, or alkoxy groups. The amine itself may be cyclic or acyclic. The amine may be a primary, secondary, or tertiary amine. The amine may also be a quaternary amine (e.g., a trimethylammonium group with a fourth bond to the polysiloxane chain) and thus bear a permanent positive charge. The amine may also be converted to an amidine group, which is more basic than a simple amine.

The polysiloxane backbone may, in certain embodiments, be substituted with an acidic moiety instead of an amine. Preferred acids are carboxylic and sulfonic acids. These acids would protonate amines or other bases added to the polysiloxane polymer to form ionic bonds and influence the viscosity and other properties of the material. Such "reversed" polysiloxane materials can achieve similar results as those systems in which the amine or other base is appended to the polysiloxane backbone. Moreover, monovalent and divalent metal cations may be added to these systems, providing another basis for influencing the properties of the compositions.

Protonation of the amine functional groups of the polysiloxane by added acid causes the development of a three-dimensional network mediated by electrostatic interactions. Such a network is termed an "interpenetrating network" and has different and advantageous properties compared with intimate mixtures of polymers. Preferred acids are carboxylic acids or di-carboxylic acids, for example, formic acid, ethanoic acid, propionic acid, pentanoic acid, hexanoic acid, trifluoroacetic acid, chloroacetic acid, dichloroacetic acid, trichloroacetic acid, methoxyacetic acid, acrylic acid, methacrylic acid, benzoic acid, vinylbenzoic acid, oxalic acid, malonic acid, succinic acid, glutaric acid, adipic acid, azelaic acid, phthalic acid isomers, a perylene dicarboxylic acid, a nitrobenzoic acid, and a polymer containing acidic groups Other preferred acids include sulfonic acids such as methanesulfonic acid, trifluoromethanesulfonic acid, benzenesulfonic acid, p-toluenesulfonic acid, taurine, and sulfonic acid-substituted ion exchange resins (e.g., Nafion). Mineral acids such as HCl, HBr, HI, HNO$_3$, H$_2$SO$_4$, H$_3$PO$_4$, B(OH)$_3$, HClO$_3$, and HClO$_4$ may be used.

Optically active acids or bases may be added to the basic- or acidic-functional group-containing polysiloxane. The use of optically active acids (or bases if the polysiloxane has acidic groups appended) can create chiral environments so that the resulting polymers would be useful in enantiomeric sensing and separations (via chromatography). Generally, the acid and base will be in an approximately stoichiometric (1:1) ratio, whether the amine is pendant on the polysiloxane polymer or the acid is pendant on the polymer. The ratio (amine:acid) may also be altered to influence the average protonation state of the amine functional groups, and may be 1.1:1, 2:1, 3:1, 4:1, or greater than 4:1. In certain embodiments, the ratio of acid:amine is 1.1:1, 2:1, 3:1, 4:1, or greater than 4:1.

Poly((aminofunctional alkoxy)-alkylsiloxane) compounds can have a variety of uses. For example, such compounds may be useful as a component of a coating composition. Depending on the particular application, a poly((aminofunctional alkoxy)-alkylsiloxane) compound may be used by itself to form a coating or may be formulated with other components known to those of skill in the art to form the coating composition. For example, a poly((aminofunctional alkoxy)-alkylsiloxane) may act as a crosslinking agent and/or curing accelerator in a coating composition, e.g., in an epoxy-based coating composition.

In another embodiment, a poly((aminofunctional alkoxy)-alkylsiloxane) compound may be used as a "primer" component in a coating system (e.g., to adhere a topcoat to a substrate). The primer containing the poly ((aminofunctional alkoxy)-alkylsiloxane) and a topcoat (e.g., polyurethane may be applied to a substrate according to the following exemplary method. A substrate (e.g., aluminum 2024-T3) may be treated by cleaning its surface with a solvent (e.g., acetone). The primer may be applied to the substrate "neat" with an applicator such as a "draw down" bar. The primer may be dried at ambient temperature for about one day, and cured at about 45 C for about five hours. The topcoat may be applied to the primer with an applicator such as a "draw down" bar. The topcoat may be dried at ambient temperature for about one day, and subsequently cured at an elevated temperature (e.g., at about 45-50° C. for a period of hours).

Other uses for the poly((aminofunctional alkoxy)-alkyl-siloxane) compounds include applications in the production of adhesives, catalyst supports, ionically conductive materials, liquid crystals, crosslinking agents, conductive and electroluminescent polymers, electrochemical sensing devices, and nonlinear optical chromophores.

It is also contemplated that the materials of the present invention may be used as controlled-release systems, e.g., as controlled-release drug delivery systems. The rate of delivery of a captured substance, or guest molecule, may be controlled by the degree of cross-linking present in the polysiloxane.

Many functionalized polysiloxane materials are commercially available. They may also be prepared synthetically by methods known in the art (see, e.g., U.S. Pat. No. 6,482,912, hereby incorporated by reference).

The present aminofunctional alkoxy polysiloxane compound can be a linear and/or cyclic alkoxy polysiloxane. As used herein, the term "aminofunctional alkoxy polysiloxane compound" refers to an alkoxy substituted polysiloxane compound which includes one or more aminofunctional alkoxy groups. For the purposes of this application, the term aminofunctional alkoxy group refers to groups which include at least one basic nitrogen atom and encompasses groups resulting from the removal of a hydroxyl hydrogen atom from an amino functional alkanol (e.g., —O—$CH_2CH_2$—O—$CH_2CH_2NH_2$), an amino functional cycloalkanol, and/or an amino functional hydroxy-substituted aryl compound (e.g., —O—$C_6H_4$—O—$CH_2CH_2NH_2$).

The siloxane subunits may not all contain an aminofunctional alkoxy group. In certain embodiments, a majority of the siloxane subunits of the polymer include an aminofunctional alkoxy group. Polysiloxanes where not all of the siloxane subunits of the polymer include the same substituents polymer (with the exception of the terminal subunits) are referred to herein as "polysiloxane copolymers." As used herein, such "copolymers" can have two or more different siloxane subunits. Polysiloxane copolymers can be formed by reacting a mixture of two alcohols, e.g., a mixture of 2-aminoethanol and ethanol, with a polyhydrosiloxane. Generally, the different siloxane subunits are randomly distributed in a polysiloxane copolymer (a "random copolymer"). However, by using appropriate synthetic methods known to those of skill in the art, polysiloxane copolymers in which the different siloxane subunits are present in "blocks" of two or more identical adjacent subunits can also be produced ("block copolymers"). The present polysiloxane copolymers typically have a ratio of siloxane subunits containing an aminofunctional alkoxy group to subunits which do not include an aminofunctional alkoxy group of about 20:1 to 1:20.

The term "acid" as used herein may include any inorganic or organic acid. The term "base" as used herein may include any inorganic or organic Bronsted or Lewis base selected from those mentioned above in addition to non-pharmaceutically acceptable bases that are efficacious in organic chemistry. Particularly preferred organic bases are isopropylamine, diethylamine, ethanolamine, trimethylamine, diisopropylethylamine (DIPEA), dicyclohexylamine, 1,4-diazabicyclo[2.2.2]octane (DABCO), 1,8-Bis(dimethylamino)naphthalene (Proton Sponge), and 1,8-Diazabicyclo[5.4.0]undec-7-ene (DBU).

The compounds of the invention may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "alkyl" as used herein is intended to include linear, branched, or cyclic hydrocarbon structures and combinations thereof. Lower alkyl (or haloalkyl) refers to alkyl (haloalkyl) groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. More preferred alkyl groups are those of $C_{12}$ or below. Cycloalkyl is a subset of alkyl and includes cyclic hydrocarbon groups of from 3 to 12 carbon atoms. Examples of cycloalkyl groups include c-propyl, c-butyl, c-pentyl, norbornyl, adamantyl and the like. The terms "alkenyl" and "alkynyl" have identical chain lengths as mentioned above for "alkyl", but have one or more double or triple bonds in the carbon chain or at the two terminal positions of the carbon chain, respectively. "Alkylene" refers to the same residues as alkyl, but having two points of attachment. Examples of alkylene include ethylene (—$CH_2CH_2$—), propylene (—$CH_2CH_2CH_2$—), dimethylpropylene (—$CH_2C(CH_3)_2CH_2$—) and cyclohexylpropylene (—$CH_2CH_2CH(C_6H_{13})$—). When an alkyl residue having a specific number of carbons is named, all geometric isomers having that number of carbons are intended to be encompassed; thus, for example, "butyl" is meant to include cyclobutyl, n-butyl, sec-butyl, isobutyl and t-butyl; "propyl" includes cyclopropyl, n-propyl and isopropyl.

"Alkoxy" or "alkoxyl" refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower alkoxy refers to groups containing one to four carbons.

"Acyl" refers to groups of from 1 to 8 carbon atoms of a straight, branched or cyclic configuration, or a combination of any such configurations, attached to the parent structure through a carbonyl functionality. Such acyl groups can be saturated or unsaturated, and aromatic or non-aromatic. One or more carbons in the acyl residue can be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower acyl refers to groups containing one to four carbons.

"Aryl" means a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene, and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

"Aralkyl" refers to a residue in which an aryl moiety is attached to an alkyl residue. Examples are benzyl, phenethyl, phenylvinyl, phenylallyl and the like.

"Oxaalkyl" and "oxaaralkyl" refer to alkyl and aralkyl residues in which one or more methylenes have been replaced by oxygen. Examples of oxaalkyl and oxaalkylaryl residues are ethoxyethoxyethyl (3,6-dioxaoctyl), benzyloxymethyl and phenoxymethyl; in general, glycol ethers, such as polyethyleneglycol, are intended to be encompassed by this group.

"Heteroaralkyl" refers to a residue in which a heteroaryl moiety is attached to the parent structure via an alkyl residue. Examples include furanylmethyl, pyridinylmethyl, pyrimidinylethyl and the like.

"Heterocyclyl" means a cycloalkyl or aryl residue in which one to four of the carbons is replaced by a heteroatom, such as oxygen, nitrogen or sulfur. Examples of heterocycles that fall within the scope of the invention include imidazoline, pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. "N-heterocyclyl" refers to a nitrogen-containing heterocycle as a substituent residue. The term heterocyclyl encompasses heteroaryl, which is a subset of heterocyclyl. Examples of N-heterocyclyl residues include 4-morpholinyl, 4-thiomorpholinyl, 1-piperidinyl, 1-pyrrolidinyl, 3-thiazolidinyl, piperazinyl and 4-(3,4-dihydrobenzoxazinyl). Examples of substituted heterocyclyl include 4-methyl-1-piperazinyl and 4-benzyl-1-piperidinyl.

Substituted alkyl, aryl and heteroaryl refer to alkyl, aryl or heteroaryl wherein one or more hydrogen atom(s) is replaced with alkyl, halogen, hydroxy, alkoxy, alkylenedioxy (e.g., methylenedioxy) fluoroalkyl, carboxy (—COOH), carboalkoxy (i.e., acyloxy RCOO—), carboxyalkyl (—COOR), carboxamido, sulfonamidoalkyl, sulfonamidoaryl, aminocarbonyl, benzyloxycarbonylamino (CBZ-amino), cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, substituted heterocyclyl, phenoxy, benzyloxy, or heteroaryloxy. For the purposes of the present invention, substituted alkyl also includes oxaalkyl residues, i.e., alkyl residues in which one or more carbons has been replaced by oxygen. Preferred substitutions include alkyl, alkenyl, alkynyl, halogen, hydroxy, alkoxy, fluoroalkyl, cyano, carbonyl, nitro, dialkylamino, alkylamino, amino, alkylthio, aralkyl, heteroaryl, and heterocyclyl.

"Halogen" refers to fluorine, chlorine, bromine or iodine. Fluorine, chlorine and bromine are preferred. Dihaloaryl, dihaloalkyl, trihaloaryl, etc., refer to aryl and alkyl substituted with a plurality of halogens, but not necessarily a plurality of the same halogen; thus 4-chloro-3-fluorophenyl is within the scope of dihaloaryl.

The terms "solvent", "inert organic solvent" or "inert solvent" mean a solvent inert under the conditions of the reaction being described in conjunction therewith. Solvents employed in synthesis of the compounds of the invention include, for example, methanol, acetone, water, acetonitrile, 1,4-dioxane, dimethylformamide, benzene, toluene, tetrahydrofuran, chloroform, methylene chloride (or dichloromethane), diethyl ether, tert-butyl methyl ether (TBME), pyridine and the like, as well as mixtures thereof. Unless specified to the contrary, the solvents used in the reactions of the present invention are inert organic solvents.

As used herein, the term "hydroxyl" means —OH.

As used herein, the term "nitro" means —NO$_2$.

As used herein, the term "thiol" means —SH.

As used herein, the term "sulfonyl" means —SO$_2$—.

As used herein, the term "disulfide" refers to any chemical compound that comprises a covalently linked pair of sulfur atoms (disulfide bond), e.g., diphenyl disulfide (C$_6$H$_5$—S—S—C$_6$H$_5$).

The terms "amine" and "amino" are art-recognized and refer to both unsubstituted and substituted amines, e.g., a moiety that can be represented by the general formula:

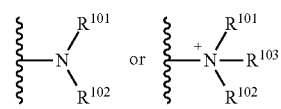

wherein $R^{101}$, $R^{102}$ and $R^{103}$ each independently represent hydrogen, alkyl, alkenyl, alkynyl, aryl, heteroaryl, —(CH$_2$)$_m$R$^{200}$, wherein m is an integer 1-10 and $R^{200}$ represents a group permitted by the rules of valence, such as hydrogen, alkyl, alkenyl, alkynyl, aryl, and heteroaryl. An "amine" or "amino" moiety may be a cyclic amine (e.g., piperidine or quinine)

The term "amino" also includes "acylamino," which is art-recognized and refers to a moiety that can be represented by the general formula:

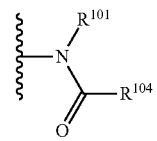

wherein $R^{101}$ is as defined above, and $R^{104}$ represents hydrogen, alkyl, alkenyl, alkynyl, aryl, heteroaryl or —(CH$_2$)$_m$R$^{200}$, wherein m and $R^{200}$ are defined above.

The term "amido" is art-recognized as an amino-substituted carbonyl and includes a moiety that can be represented by the general formula:

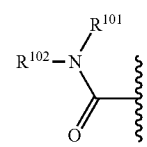

wherein $R^{101}$ and $R^{102}$ are as defined above. Preferred embodiments of the amide will not include those which are unstable.

The term "alkylthio" refers to an alkyl group, as defined above, having a sulfur radical attached thereto. In preferred embodiments, the "alkylthio" moiety is represented by 200, one of —S-alkyl, —S-alkenyl, —S-alkynyl, and —S—(CH$_2$)$_m$—R wherein m and $R^{200}$ are defined above. Representative alkylthio groups include methylthio and ethylthio.

The term "carbonyl" is art-recognized and includes such moieties as can be represented by the general formula:

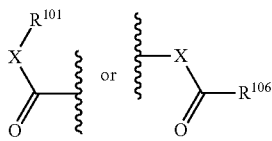

wherein X is a bond or represents an oxygen or a sulfur, and $R^{105}$ represents a hydrogen, alkyl, alkenyl, alkynyl, aryl, heteroaryl or —$(CH_2)_m R^{200}$, wherein m and $R^{200}$ are defined above, or a pharmaceutically acceptable salt, and $R^{106}$ represents hydrogen, alkyl, alkenyl, alkynyl, aryl, heteroaryl or —$(CH_2)_m R^{200}$, wherein m and $R^{200}$ are defined above. Where X is oxygen and $R^{105}$ or $R^{106}$ is not hydrogen, the formula represents an "ester". Where X is oxygen and $R^{105}$ is as defined above, the moiety is referred to herein as a carboxyl group, and particularly when $R^{105}$ is hydrogen, the formula represents a "carboxylic acid". Where X is oxygen and $R^{106}$ is hydrogen, the formula represents a "formate". In general, where the oxygen atom of the above formula is replaced by sulfur, the formula represents a "thiocarbonyl" group. Where X is a sulfur and $R^{105}$ or $R^{106}$ is not hydrogen, the formula represents a "thioester." Where X is sulfur and $R^{105}$ is hydrogen, the formula represents a "thiolcarboxylic acid." Where X is a sulfur and $R^{106}$ is hydrogen, the formula represents a "thiolformate." On the other hand, where X is a bond and $R^{105}$ is not hydrogen, the above formula represents a "ketone" group. Where X is a bond, and $R^{106}$ is hydrogen, the above formula represents an "aldehyde" group.

The terms "alkoxyl" or "alkoxy" as used herein refer to an alkyl group, as defined above, having an oxygen radical attached thereto. Representative alkoxyl groups include methoxy, ethoxy, propyloxy, t-butoxy and the like.

An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, and —$(CH_2)_m$—$R^{200}$, where m and $R^{200}$ are as defined above.

The term "heteroatom" as used herein means an atom of any element other than carbon or hydrogen. Preferred heteroatoms are nitrogen, oxygen, sulfur, phosphorus and selenium. In one embodiment, a heteroatom is selected from nitrogen, oxygen, and sulfur. In one embodiment, a heteroatom is selected from nitrogen and oxygen. In one embodiment, a heteroatom is nitrogen. In one embodiment, a heteroatom is oxygen.

An aspect of the invention is a method of preparing a composition of the invention, comprising the step of combining a polysiloxane comprising a plurality of pendant amines; and an acid selected from the group consisting of carboxylic acids, sulfonic acids, HCl, HBr, HI, $HNO_3$, $H_2SO_4$, $H_3PO_4$, $B(OH)_3$, $HClO_3$, and $HClO_4$.

In one embodiment, the method further comprises the step of irradiating the composition.

An aspect of the invention is a method of preparing a composition of the invention, comprising the step of combining a polysiloxane comprising a plurality of pendant acids selected from the group consisting of carboxylic acids and sulfonic acids; and an amine.

In one embodiment, the method further comprises the step of irradiating the composition.

An aspect of the invention is a battery, comprising a composition of the invention.

In one embodiment, the battery further comprises a plurality of lithium ions. An aspect of the invention is a composition for controlled release of a compound, comprising a composition of the invention; and the compound.

In one embodiment, the compound is an active pharmaceutical ingredient.

EXEMPLIFICATION

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. The invention now being generally described, it will be more readily understood by reference to the following, which is included merely for purposes of illustration of certain aspects and embodiments of the present invention, and is not intended to limit the invention.

Example 1

General Procedures; 6-7PSil Carboxylates

Materials. (3-Aminopropyl)methylsiloxane-co-dimethysiloxane copolymer with 6-7% monomer units with amino groups (6-7PSil; Gelest, Inc.; characterization data from supplier: by >205° C., mp<−60° C., molecular weight: 3000-6000, viscosity: 0.08-0.12 Pa.$) and N-(2-aminoethyl)-3-aminopropylmethylpolysiloxane ($D_2EDA$; Siltech, Inc.; characterization data from supplier: molecular weight: 1700 and one primary amino and one secondary amino group in 23% of the monomer units) were used as received. Acetic acid (EM Science, 99.7%), propionic acid (Mallinckrodt, AR, 99.95%), trifluoroacetic acid (Acros, 99%), benzoic acid (Sigma-Aldrich, 99%), acrylic acid (Aldrich, 99%), oxalic acid (Acros, 98%), malonic acid (Sigma-Aldrich, 99%), succinic acid (Aldrich, 99+%), glutaric acid (Aldrich, 99%), azelaic acid (Aldrich, 98%), succinic acid (Aldrich, 99+%), glutaric acid (Aldrich, 99%), azelaic acid (Aldrich, 98%), vinylbenzoic acid (Fisher, 97%), azobisisobutyronitrile (AIBN, Aldrich, 98%), tert-butylamine (Aldrich, 98%), tributylamine (Aldrich, 98%) 1,4-dioxane (Sigma-Aldrich, anhydrous, 99.8%), diethyl ether (EMD, >98%), ethyl acetate (Sigma-Aldrich, ACS reagent, >99.5%), chloroform (Sigma-Aldrich, ACS reagent, >99.8%), 2-hydroxy-2-methyl-1-phenyl-propan-1-one (Darocur 1173, Ciba), and methylene chloride (Fisher Scientific, HPLC Grade) were used as received.

Instrumentation. Thermogravimetric analysis (TGA) measurements were performed on a TGA Q50 thermogravimetric analyzer (TA Instruments, New Castle, Del.) interfaced to a computer. Samples of 2-10 mg were heated at 10° C./min under a slow stream of nitrogen. Differential scanning calorimetry (DSC) measurements were performed on a Q200 calorimeter (TA Instruments, New Castle, Del.) interfaced to a TA Thermal Analyst 3100 controller that was connected to an RCS90 cooling system. Samples were placed in open Tzero pans. Both the heating and cooling rates were 10° C./min and measurements were made under a slow stream of nitrogen. Rheological measurements were performed with an Anton Paar Physica MCR 301 strain-controlled rheometer (Anton Paar GmbH, Graz, Austria), equipped with a Peltier temperature controller and parallel plates (25 mm diameter) at 25° C. The data were collected using Rheoplus/32 Service V3.10 software. Before data were recorded, each sample was placed directly onto the steel base plate, and the upper parallel steel plate was moved into the 0.5 mm initial gap and contact with the upper sample surface, after which any excess substrate sample was removed. Then, the samples were kept undisturbed at 25° C. for 5 min to ensure thermal equilibration. For viscosity and moduli measurement, 25 data points were recorded. Duplicate measurements were performed with new samples. $^1$H NMR spectra were recorded on a Varian 400 MHz spectrometer (Varian Inc. CA, USA) with VnmrJ software using tetramethylsilane as the internal standard. Each spectrum was based upon 64 FIDs.IR spectra were recorded on a Nicolet 380 FT-IR spectrometer (Thermo Electron, MA, USA) with Omnic software (average of 32 spectra with 4 cm$^{-1}$ resolution). Liquid samples were placed as films between NaCl windows. All experiments were conducted at room temperature unless indicated otherwise.

Adhesion test. Room temperature adhesion of synthesized polymers to surfaces was measured by two different methods. In method 1, based on extensional rheology, data were collected on the rheometer and analyzed with Rheoplus/32 Service V3.10 software. Samples were placed directly onto the steel base plate, and the upper parallel steel plate was moved to an initial 0.5 mm gap so that the sample was in complete contact with the upper plate. After excess sample was removed, the samples were equilibrated at 25° C. for 5 min. Then, the top plate was lifted vertically at 1 µm/s until the normal force did not change (i.e., the film was broken completely). The normal force response in this process was recorded by the rheometer, and the maximum force is reported. Additional measurements were performed with new aliquots of the same samples.

Method 2 employed an Instron 3345 (Instron Co. MA, USA) universal testing machine, with a 5 kN load, controlled by Bluehill software in the extension mode according to the ISO 4587:2003 protocol. The sample holder was composed of three glass slides (10.0 cm×2.50 cm×2.38 mm). One end of two of the plates was attached vertically to the upper and lower fixtures of the machine. The third slide was placed parallel to and overlapping the other two. One-half of the third plate was bonded by epoxy adhesive (ATACS, 5104/4103) to one of the other plates and a film of 1.25 cm×2.50 cm cross-sectional area and ca. 100 µm thickness was placed in contact with the other half and one-half of the third plate. The film thickness was controlled by placing a polyethylene film spacer (DuPont Sclairfilm LLDPE Film, 4 mils) between the two plates. Thereafter, the upper grip was pulled vertically at 20 mm/min until the polymer layer was broken totally. The force during the vertical motion was recorded as a function of extension distance and time, and the maximum force is reported.

The data shown in the Figures are averages of three trials, and the error bars represent one standard deviation.

Syntheses of ammoniumpolysiloxane carboxylates. The amine contents were calculated to be $8.50 \times 10^{-4}$ mol/g (6.5% amine content) for 6-7PSil by potentiometric titrations with trifluoroacetic acid in ethanol and $4.46 \times 10^{-3}$ mol/g (one primary amino and one secondary amino group in 23% of the monomer units) for D$_2$EDA as calculated from the amine value supplied by the manufacturer.

Ammoniumpolysiloxane carboxylates with a solid acid (benzoic acid, oxalic acid, malonic acid, succinic acid, glutaric acid, or azelaic acid) were synthesized by refluxing and stirring known weights of aminopolysiloxane and a carboxylic acid and methylene chloride (2-3 times the mass of polysiloxane) for 3 h. The solvent was removed by placing the sample sequentially on a rotary evaporator, under dynamic reduced pressure at 150 mm Hg for >24 h at room temperature, and under dynamic reduced pressure of 0.5 mm Hg for 3 h at 40-50° C. Ammoniumpolysiloxane carboxylates with a liquid acid (acetic acid, propionic acid, trifluoroacetic acid, acrylic acid, or methacrylic acid) were synthesized by stirring known weights of aminopolysiloxane, and a carboxylic acid at room temperature for 1 h, followed by refluxing and stirring for 3 h after adding methylene chloride (2-3 times mass of polysiloxane). The solvent from the reaction mixtures was removed sequentially on a rotary evaporator under dynamic reduced pressure of 150 mm Hg for >24 h at room temperature, and under dynamic reduced pressure of 0.5 mm Hg for 3 h at 40-50° C.

Synthesis of poly(acrylic acid). Acrylic acid (613 mg) and 300 mg Darocur 1173 (as photoinitiator) in 10 g 1,4-dioxane was sealed in a Pyrex vial and irradiated for 1 h. The radiation led to some warming of the sample. It was cooled to room temperature and poured slowly into 200 mL of stirred acetone. The light yellow solid that precipitated was washed with three 30 mL aliquots of acetone and dried at 50° C. under dynamic reduced pressure of 150 mm Hg for >24 h to yield 78% of polymer.

Synthesis of poly(vinylbenzoic acid). Nitrogen gas was bubbled through a solution of 1.0 g vinylbenzoic acid and 20 mg AIBN (azobisbutyronitrile) in 10 g 1,4-dioxane for 30 min. The solution was stirred and heated at 85-90° C. for 3 h under a nitrogen atmosphere. The solution was cooled to room temperature and poured slowly into 200 mL of stirred ether. The yellow solid that precipitated was washed with three 30 mL aliquots of chloroform and dried at 50° C. under dynamic reduced pressure of 150 mm Hg for >24 h to yield 67% of polymer.

Irradiations. Samples for irradiation were prepared by placing an ammoniumpolysiloxane acrylate and 3 wt % Darocur 1173 (as photoinitiator) into sealed, transparent Pyrex vials under air and stirring for 10 min in the dark. The vials were irradiated with a 450 W medium pressure mercury lamp (Hanovia, PC451050) for 1 h at 8 cm distance.

Tributylamine or tert-butylamine and one molar equivalent acrylic acid at $8.50 \times 10^{-4}$ mol/g concentrations in methanol were placed in sealed Pyrex vials under air and irradiated with stirring at room temperature 1 h. White solids were obtained after removing the solvent under dynamic reduced pressure at 150 mm Hg for >24 h at 50° C.

Post-irradiation treatment protocols. In one experiment, 178 mg of an irradiated sample of 6-7PSil and acrylic acid and 15.8 g of 20 wt % trifluoroacetic acid were stirred for 3 h at 65° C. followed by filtration and removal of the liquid on a rotary evaporator. In another experiment, 270 mg of irradiated 6-7PSil and acrylic acid and 50 mL of 1 M hydrochloric acid were stirred for 3 h at 65° C. and then treated as before. Also, 100 mg of an irradiated acrylate sample and 50 mL of 0.25 M NaOH aqueous solution were stirred at room temperature for 3 h. No signals expected of a poly(acrylic acid) product or acrylic acid were discernible in the resulting $^1$H NMR spectra from these experiments.

Also, 100 mg of an irradiated 6-7PSil-acrylate sample was stirred in 50 mL of 0.25 M NaOH aqueous solution at 65° C. for 3 h, filtered, and part of the liquid was dried. The remainder of the liquid was extracted with 3×30 mL aliquots of ether, ethyl acetate, and methylene chloride sequentially. Removal of the combined organic liquids led to no discernible residue. The aqueous liquid was treated with 1 M HCl to pH=2-3 followed by extraction with the same solvents as indicated above. The organic and aqueous liquids were evaporated to residue separately; neither showed peaks indicative of an acrylate-derived material.

100 mg of an irradiated 6-7PSil-vinylbenzoate (or 6-7PSil-methacrylate) sample was stirred in 50 mL of 0.25 M NaOH aqueous solution at 65° C. for 3 h, filtered, and part of the liquid was dried. The remainder of the liquid was extracted with 3×30 mL aliquots of ether, ethyl acetate, and methylene chloride sequentially. Removal of the combined organic liquids led to no discernible residue. The aqueous liquid was treated with 1 M HCl to pH=1-2 followed by extraction with the same solvents as indicated above.

Swelling experiments. A weighed aliquot (ca. 50 mg) of polymer sample and 3 mL of a liquid were placed in a closed screw cap glass vial for 24 h. The polymer was removed, its surface was dried quickly on a piece of filter paper, and it was reweighed. The swelling ratio (S %) was calculated by following equation, where Wg and Wp are the weights of swelled and dry polymer, respectively.

$$S\% \ (w/w)=[(Wg-Wp)/Wp]\times 100\%$$

Results and discussion. 6-7PSil was used in all experiments except for FTIR measurements. Due to its higher amino content (and stronger peak absorbances in the regions of interest in the IR region), $D_2$EDA was used to synthesize and analyze an ammonium acetate (vide infra). The ammoniumpolysiloxane carboxylates from 6-7PSil and mono- and di-carboxylic acids (Scheme 1) are listed in Table 1.

Scheme 1. Ammoniumpolysiloxane carboxylates from 6-7PSil and carboxylic acids; for clarity, dimethylsiloxyl units are not shown with the di-acids.

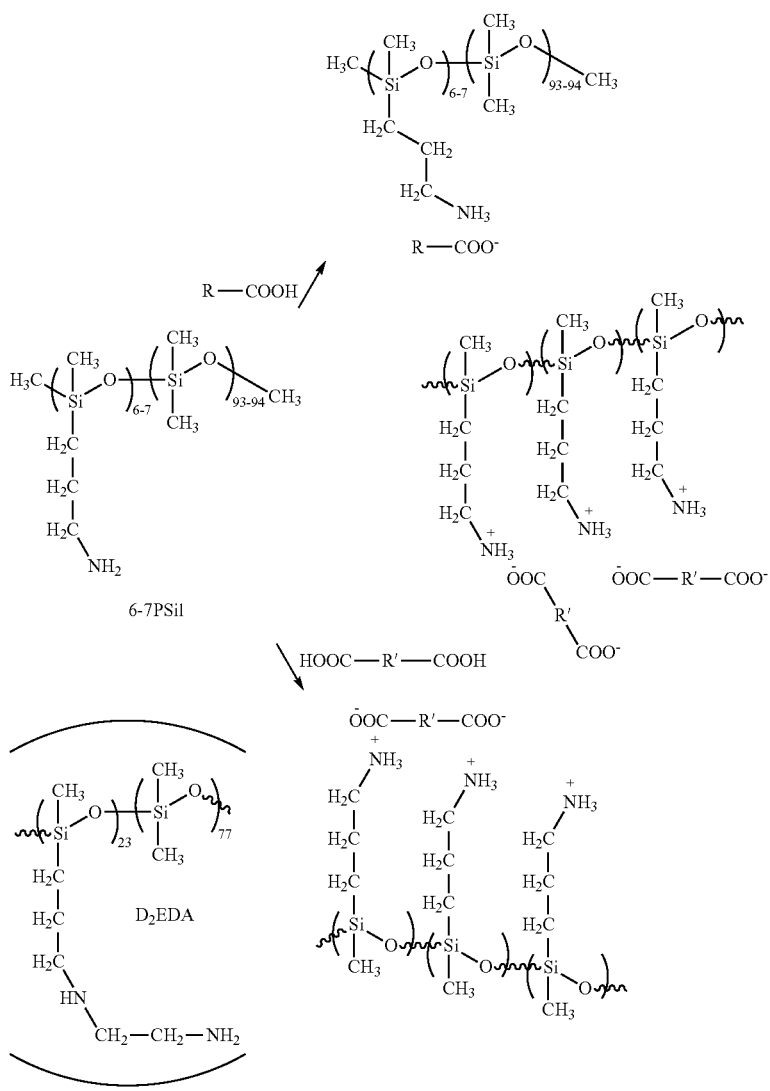

Spectroscopic evidence for the formation of the ammoniumpolysiloxane carboxylates was obtained by IR spectroscopy. Absorption peaks for the amine functional groups of 6-7PSil were too weak to be detected. Although the relevant IR peaks of $D_2EDA$, which contains ca. 23% of the monomer units with one primary and one secondary amino group, could be detected easily (FIG. 1), electrostatic repulsion between vicinal ammonium groups probably limits the fraction of them that are formed when even more than one equivalent of acetic acid was added. However, no C=O peak indicative of free acetic acid (~1706 cm$^{-1}$) and no —NH$_2$ peak (~1578 cm$^{-1}$) can be detected in the spectrum of the product from reaction between $D_2EDA$ and one equivalent of acetic acid; a peak attributed to —NH$_3^+$ (1565 cm$^{-1}$) is apparent, however.

TABLE 1

Carboxylic acids and ammoniumpolysiloxane carboxylates examined.

| Acid | R | R' | pKa(s)[1] | Salt acronym |
|---|---|---|---|---|
| Acetic | CH$_3$— | | 4.74 | PM1 |
| Propionic | CH$_3$CH$_2$— | | 4.87 | PM2 |
| Trifluoroacetic | CF$_3$— | | 0.23 | PMCF3 |
| Acrylic | H$_2$C=CH— | | 4.35 | PMAA |
| Methacrylic | H$_2$C=C(CH$_3$)— | | 4.65 | PMMA |
| Benzoic | C$_6$H$_5$— | | 4.19 | PMPh |
| Vinyl benzoic | H$_2$C=CHC$_6$H$_5$— | | 4.29 | PMVPh |
| Oxalic | | N/A | 1.27, 4.28 | PD0 |
| Malonic | | —(CH2)— | 2.83, 5.70 | PD1 |
| Succinic | | —(CH2)$_2$— | 4.19, 5.64 | PD2 |
| Glutaric | | —(CH2)$_3$— | 4.35, 5.42 | PD3 |
| Adipic | | —(CH2)$_4$— | 4.43, 5.41 | PD4 |
| Azelaic | | —(CH2)$_7$— | 4.55, 5.50 | PD7 |

Carboxylates derived from vinylbenzoic and methacrylic acids were also prepared, as detailed elsewhere.

Figure 2:
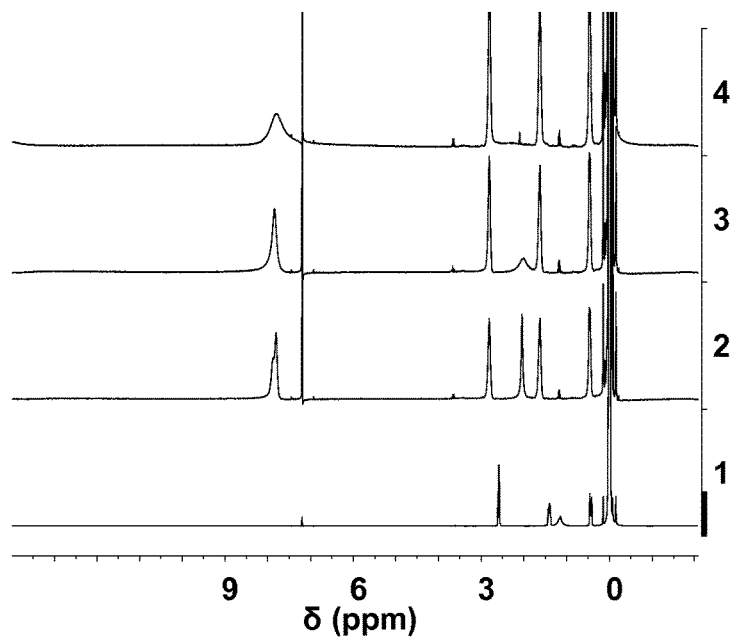
FIG. 2 depicts vertically offset $^1H$ NMR spectra of 6-7PSil without (1), and with one molar equivalent of trifluoroacetic acid in $CDCl_3$ after 0.5 h at 25° C. (2) another 0.5 h at 50° C. (3) and 1.5 h at 50° C. (4).
Figure 11:
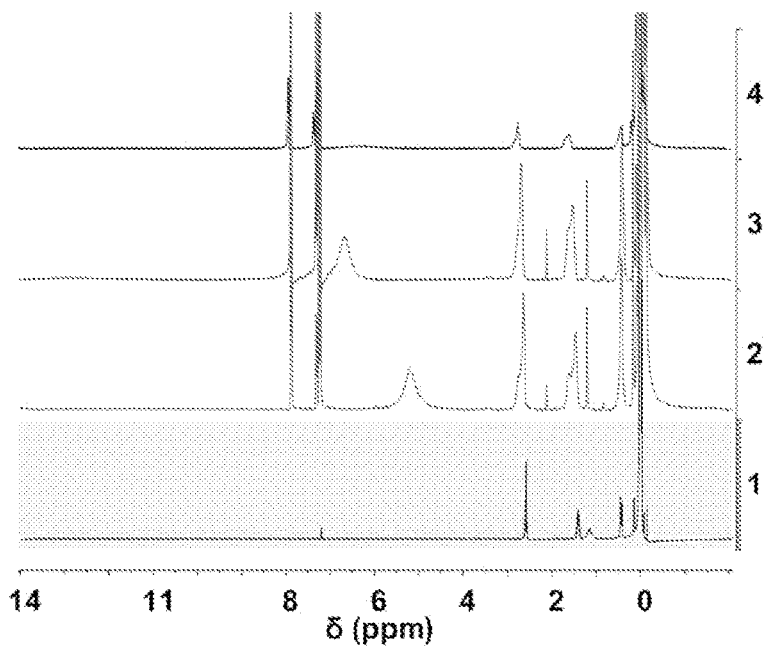
FIG. 11 depicts vertically offset $^1$H NMR spectra of 6-7PSil without (a) and with 0.5 (b), 0.75 (c) and 1.0 (d) molar equivalents of benzoic acid in CDCl$_3$.

$^1$H NMR spectra of 6-7PSil and one equivalent of trifluoroacetic acid at different times after mixing are shown in FIG. 2. At 0.5 h, the amine peak (at 1.2 ppm) was reduced significantly and two new peaks appeared at 2.0 and 7.5 ppm. At longer times, the peak at 2.0 ppm gradually decreased, but the peak at 7.5 ppm, assigned to the ammonium protons, increased and broadened. $^1$H NMR spectra of 6-7PSil with different molar equivalents of benzoic acid, a weaker acid (FIG. 11), produced analogous ammonium peaks. As the molar ratio of acid was increased, the amine peak at 1.2 ppm gradually decreased, and a new peak, which moved progressively to lower fields and broadened as the acid concentration increased, appeared.

Studies in very polar, uncharged media (such as DMSO) indicate that the strengths of acids are not as sensitive to substituent effects as they are in water (see Jaworski, J. S. *J. Chem. Soc., Perkin Trans.* 2 2000, 5, 1029-1031 and Taft, R. W. et al. *Accts. Chem. Res.* 1988, 21, 463-469). In ionic liquids (solvents that approximate the local environments experienced by carboxylic acids in 6-7PSil after conversion of the amino groups to ammonium cations), fewer data are available, and the acidity values of solutes depend upon the structure of the cationic and anionic portions of the media (see, e.g., Varinia S. et al. *J. Phys. Chem. B*, 2012, 116, 9122-9129 and Deng, H. et al. *J. Org. Chem.* 2012, 77, 7291-7298). However, it is clear that, again, the influence of substituents of a carboxylic acid on its pKa value should be attenuated with respect to values found in water. Thus, we expect that the interactions of the set of mono-acids in Table 1 with 6-7PSil will depend more on their shapes than on their pKa values in water. The dependence of the set of di-acids is more difficult to predict because electrostatic factors will vary with the distance between the carboxylic acid/carboxylate groups.

Figure 3:
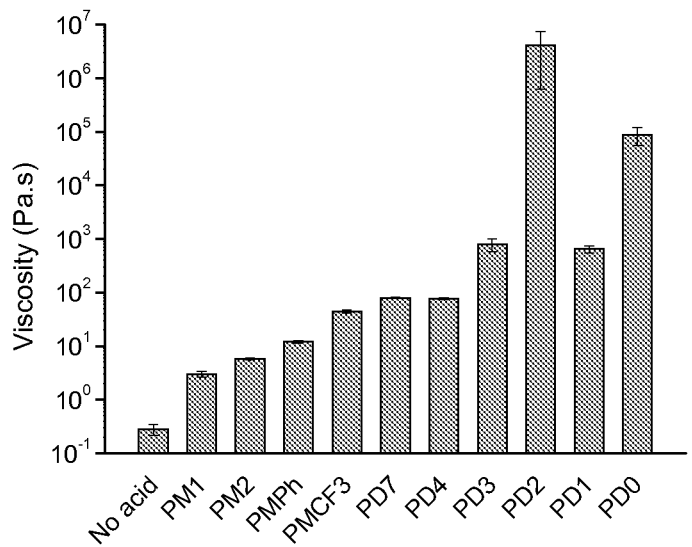
FIG. 3 depicts average viscosities over 0.1-100 Pa shear stress of 6-7PSil and its ammonium carboxylate salts.
Figure 12:
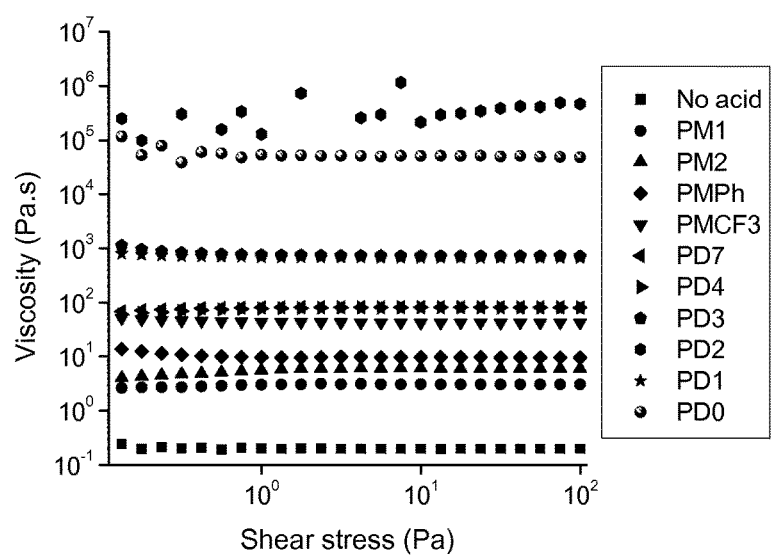
FIG. 12 depicts viscosities versus shear stress of 6-7PSil ammonium carboxylates.
Figure 13:
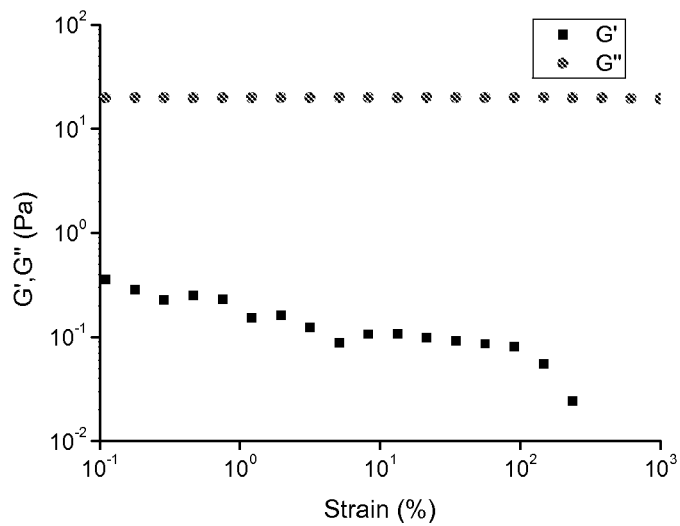
FIG. 13 depicts moduli of PM1 versus strain at 1 Hz frequency. See Table 1 for definitions of various acronyms used throughout the specification and Figures.
Figure 14:
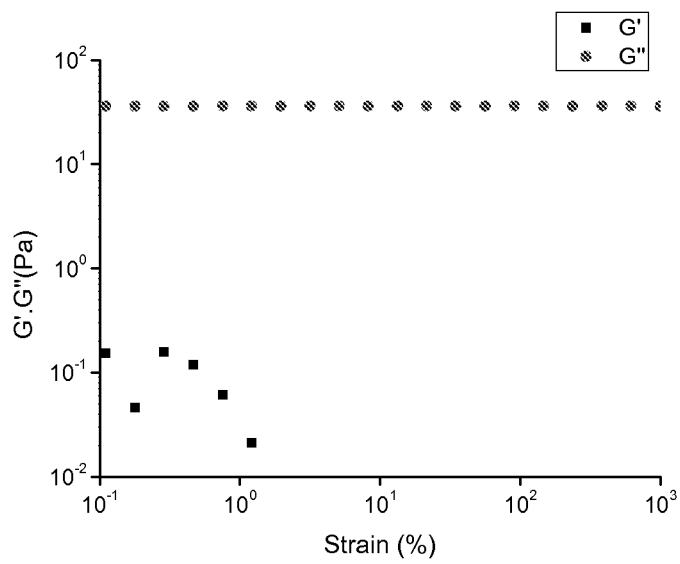
FIG. 14 depicts moduli of PM2 versus strain at 1 Hz frequency.
Figure 15:
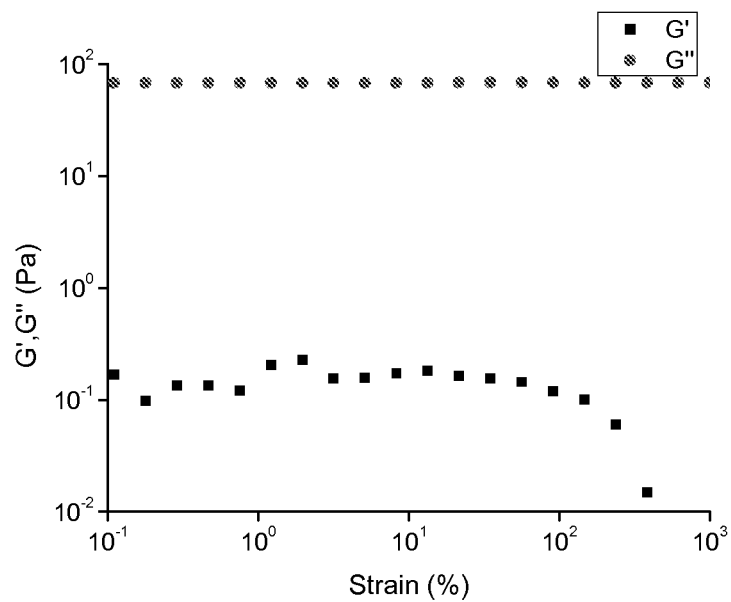
FIG. 15 depicts moduli of PMPh versus strain at 1 Hz frequency.
Figure 16:
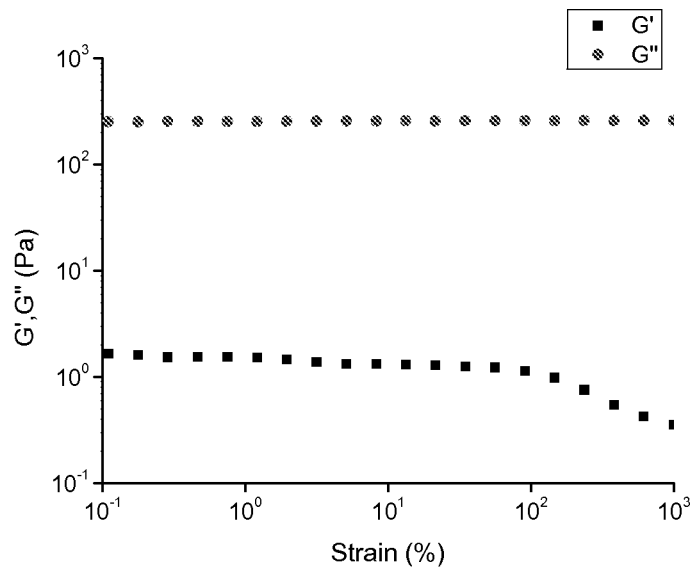
FIG. 16 depicts moduli of PMCF3 versus strain at 1 Hz frequency.
Figure 17:
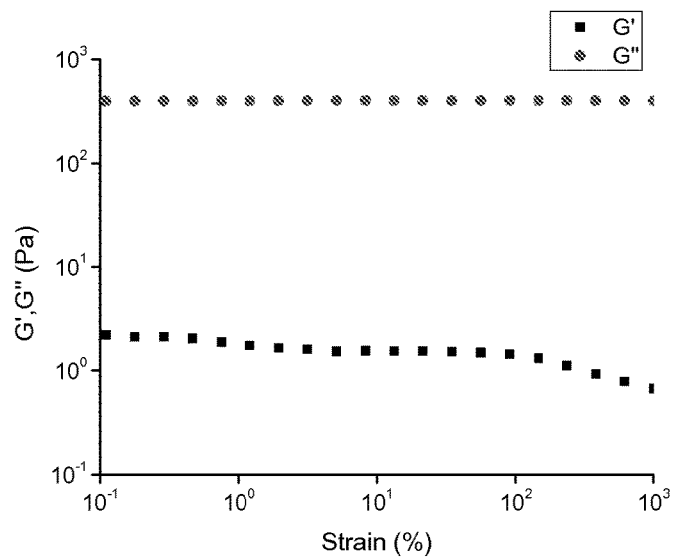
FIG. 17 depicts moduli of PDA7 versus strain at 1 Hz frequency.
Figure 18:
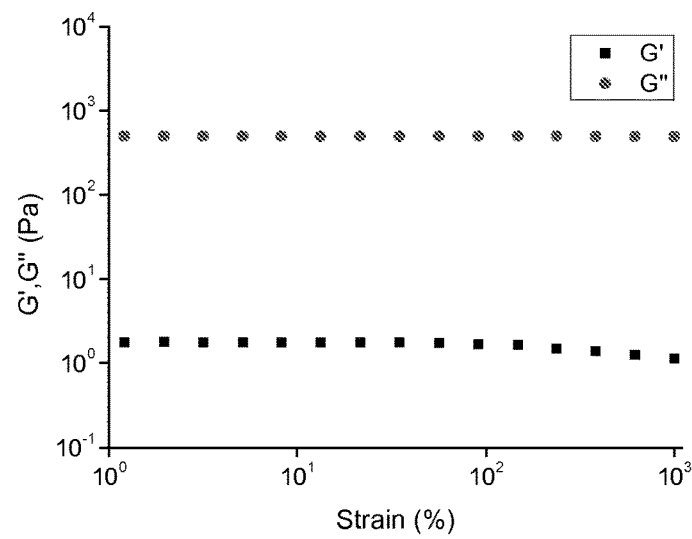
FIG. 18 depicts moduli of PD4 versus strain at 1 Hz frequency.
Figure 19:
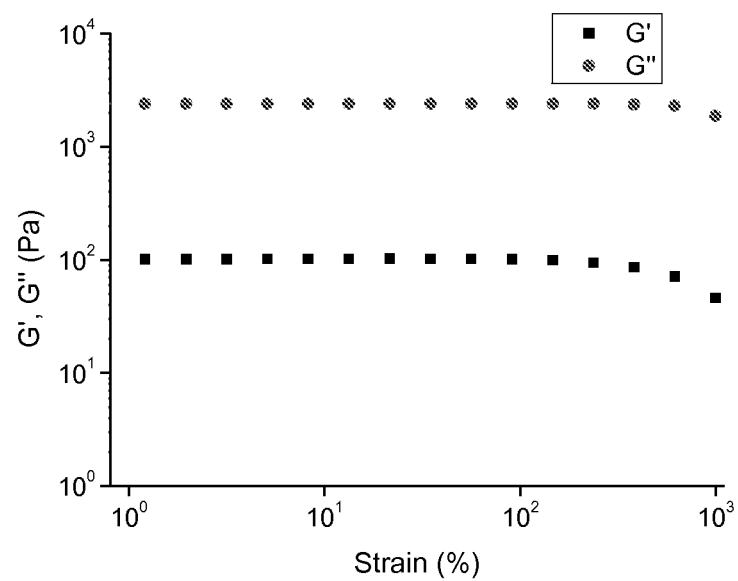
FIG. 19 depicts moduli of PD3 versus strain at 1 Hz frequency.
Figure 20:
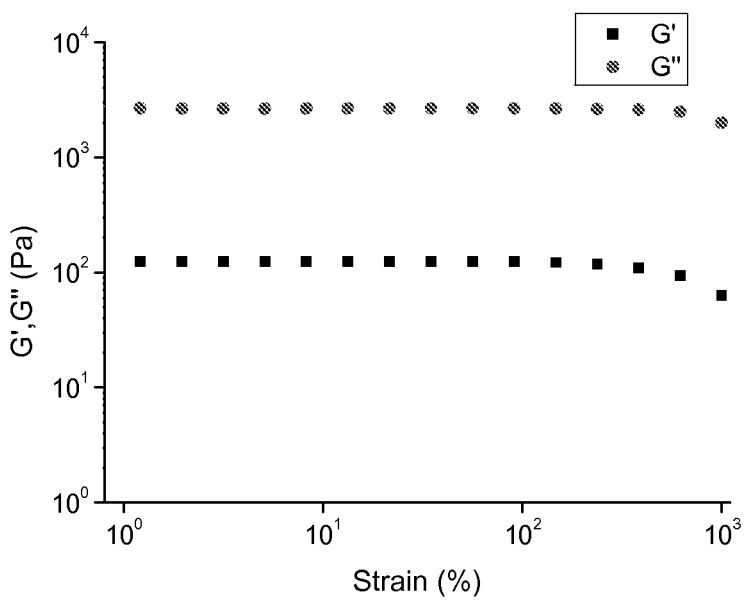
FIG. 20 depicts moduli of PD1 versus strain at 1 Hz frequency.
Figure 21:
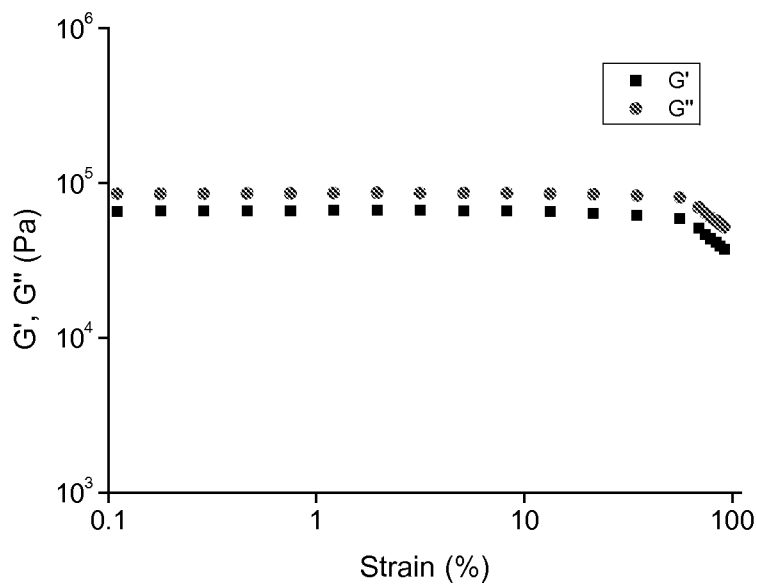
FIG. 21 depicts moduli of PD0 versus strain at 1 Hz frequency.
Figure 22:
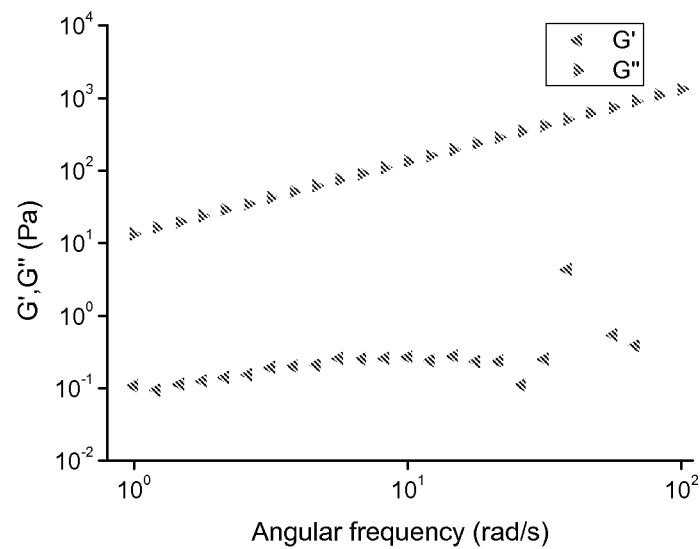
FIG. 22 depicts a frequency sweep of PMPh at 1% strain.
Figure 23:
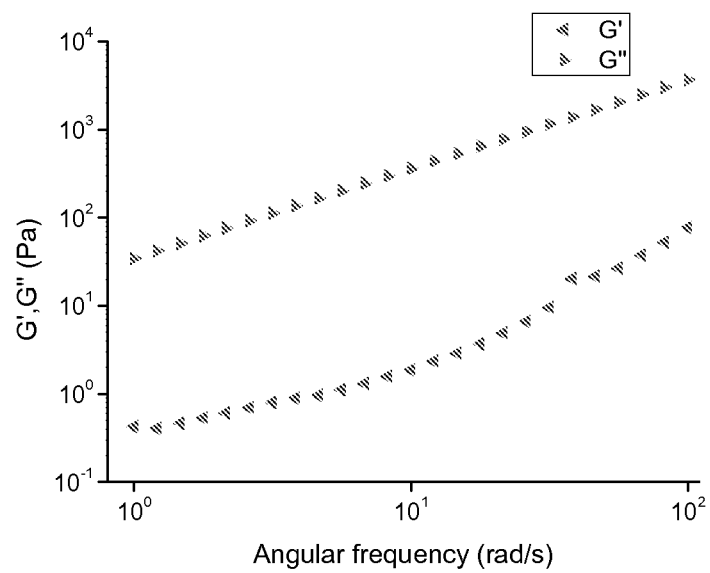
FIG. 23 depicts a frequency sweep of PMCF3 at 1% strain.
Figure 24:
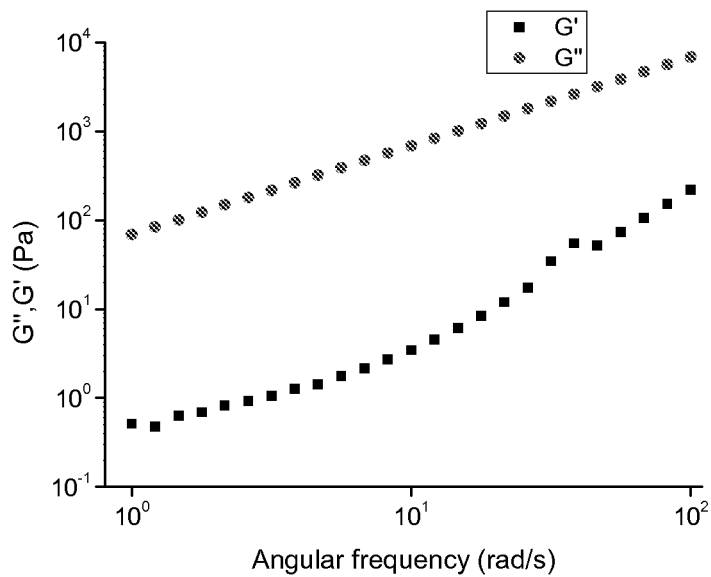
FIG. 24 depicts a frequency sweep of PD7 at 1% strain.
Figure 25:
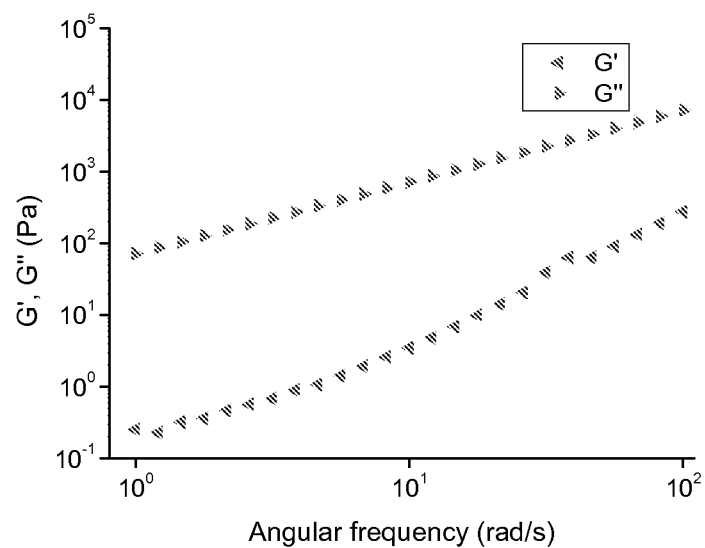
FIG. 25 depicts a frequency sweep of PD4 at 1% strain.
Figure 26:
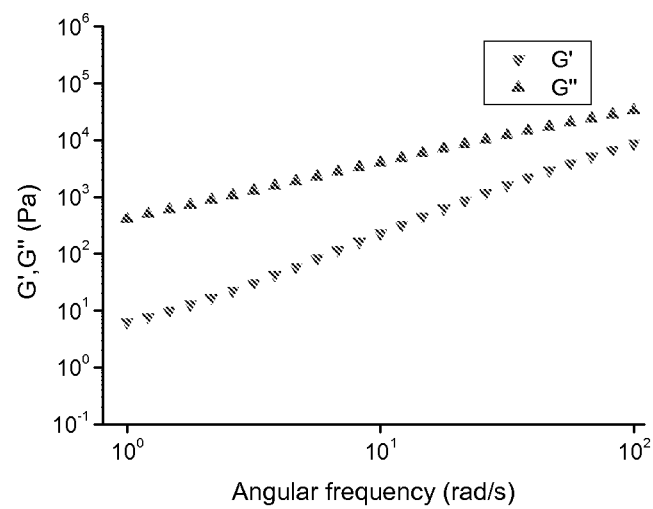
FIG. 26 depicts a frequency sweep of PD3 at 1% strain.
Figure 27:
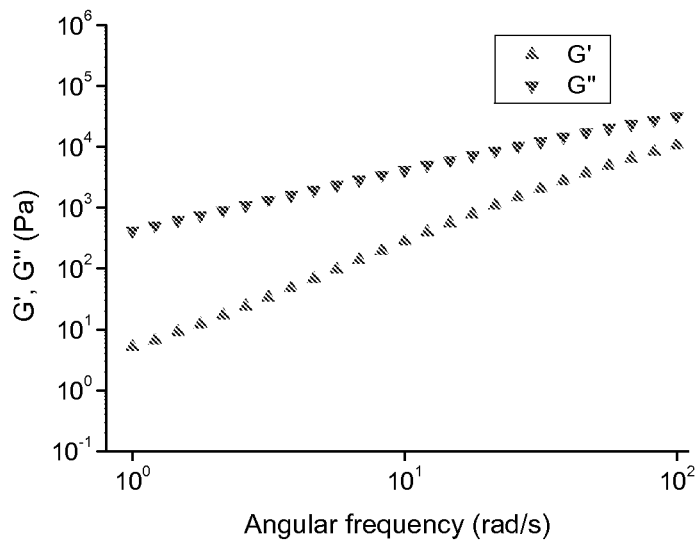
FIG. 27 depicts a frequency sweep of PD1 at 1% strain.
Figure 28:
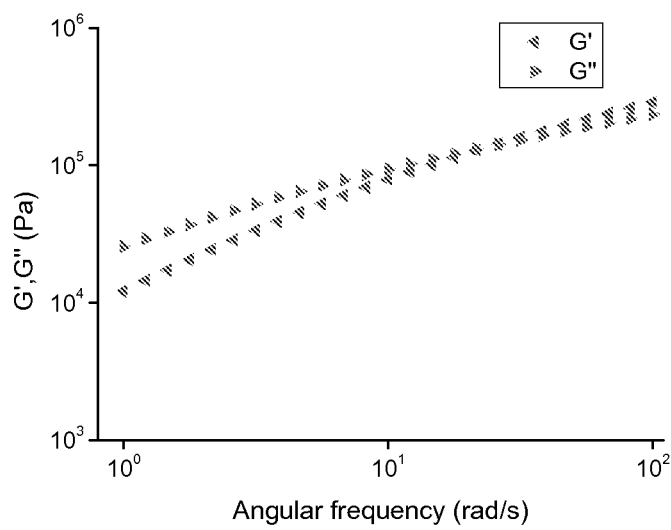
FIG. 28 depicts a frequency sweep of PD0 at 1% strain.

Electrostatic interactions, ionic crosslinks, and chain entanglements are known to alter the rheological properties of polymers. Both static and dynamic rheological investigations were performed on 6-7PSil with and without the presence of a carboxylic acid. The steady-shear viscosities of 6-7PSil and its carboxylates were independent of shear rate (FIG. 12). Their average values for the whole of the regions measured are listed in FIG. 3. The viscosity of 6-7PSil is very low, 0.2 Pa·s; much larger values were found for that of the ammonium carboxylate salts. Even the 6-7PSil salt with the structurally simplest and smallest mono-acid, acetic acid, exhibited a viscosity that is about 27 times larger than that of 6-7PSil. The viscosities of the salts increased in the order of trifluoroacetate>benzoate>propionate>acetate. We hypothesize that the larger size of the propionate and benzoate and the stronger acidity of trifluoroacetic acid increase electrostatic interactions by increasing inter-chain ionic interactions.

Viscosities of the di-acid ammonium salts were much larger than those of the mono-acid ammonium salts. However, offering a rationalization for the chain length dependence of the viscosities within the diacid-based salts is much more difficult: the viscosity of the oxalate salt (R'=no atom in Table 1) was lower than that of the succinate (R'=(CH$_2$)$_2$), but the viscosities of both the malonate (R'=CH$_2$) and glutarate salts (R'=(CH$_2$)$_3$) were lower than that of the oxalate. We conjecture that the conformation of the linking ethylene chain between the carboxylate groups in the succinate (or factors related to and convoluted with it) are responsible for its extraordinarily large viscosity. Additional experiments need to be conducted in order to discern the actual causes of the observed dependence of viscosity on chain length of the diacids.

Figure 4:
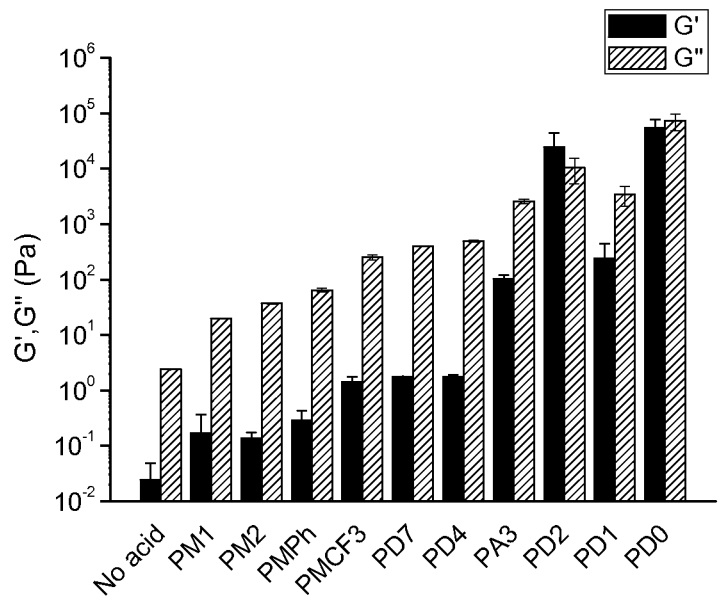
FIG. 4 depicts moduli of 6-7PSil and its ammonium carboxylates at 1.2% strain and 1 Hz frequency.
Figure 5:
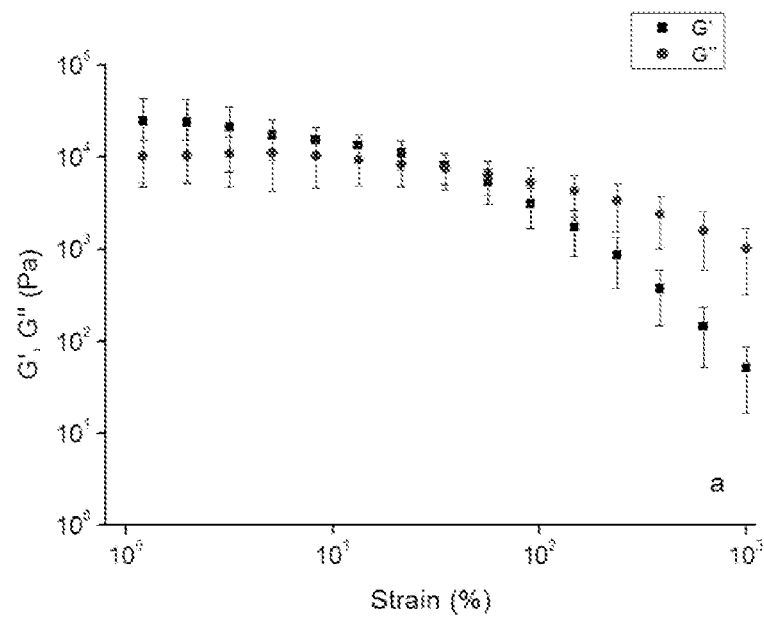
FIG. 5 depicts moduli versus strain at 1 Hz frequency (a) and frequency sweep at 1% strain (b) of PD2.
Figure 5B:
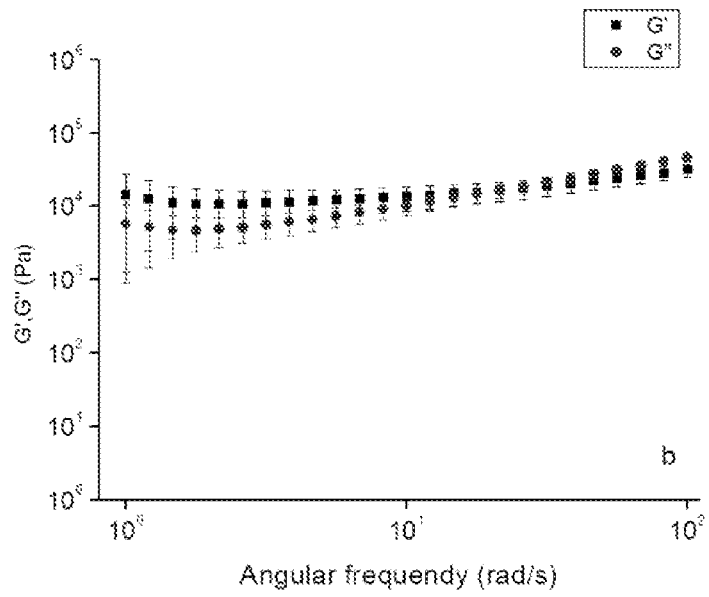

The storage modulus (G') and loss modulus (G") of 6-7PSil and its ammonium salts were also measured in strain sweeps (FIG. 5 and FIGS. 13-21), and the moduli reported in FIG. 4 are at 1.2% strain (i.e., in the linear viscoelastic regimes). The trend in these moduli follows that of the viscosities: G' and G" of the mono-acid ammoniumpolysiloxane carboxylates are higher than that of 6-7PSil and decrease in same order as the viscosities. Both G' and G" of the di-acid ammoniumpolysiloxane carboxylates are much larger than those of the mono-acid systems, and, generally, they increase as the spacer between the carboxylate groups becomes shorter (FIG. 5a). Again, succinic acid is an exception, although its moduli were not as large as those of the oxalate salt. Furthermore, none of the salts, except the succinate, behaves rheologically like a gel: G' is smaller than G" throughout the frequency range investigated (FIGS. 22-28). A frequency sweep in the linear viscoelastic region of the succinate salt showed that G' remains larger than G" at angular frequencies <31 rad/s (FIG. 5b); the ammoniumpolysiloxane succinate salt is a gel-like material at low frequencies, albeit a weak one.

Figure 29:
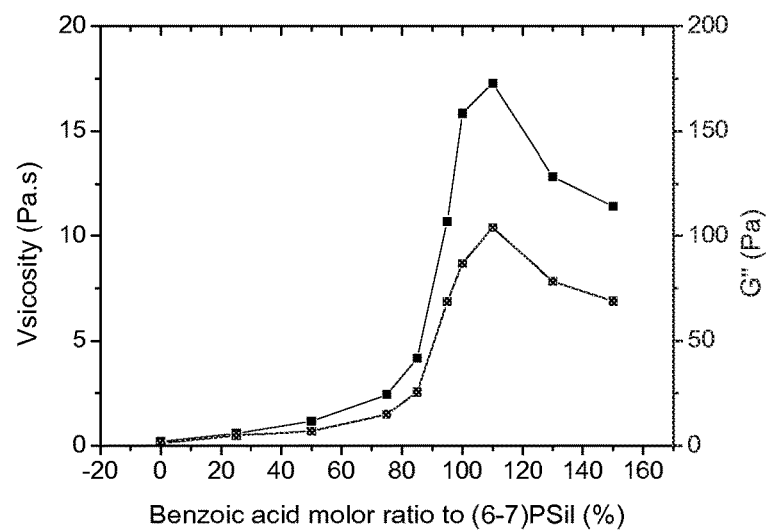
FIG. 29 depicts viscosity (top curve) and G" (bottom curve; at 1.2% strain and 1 Hz frequency) of PMPh as a function of different amounts of added benzoic acid.
Figure 30:
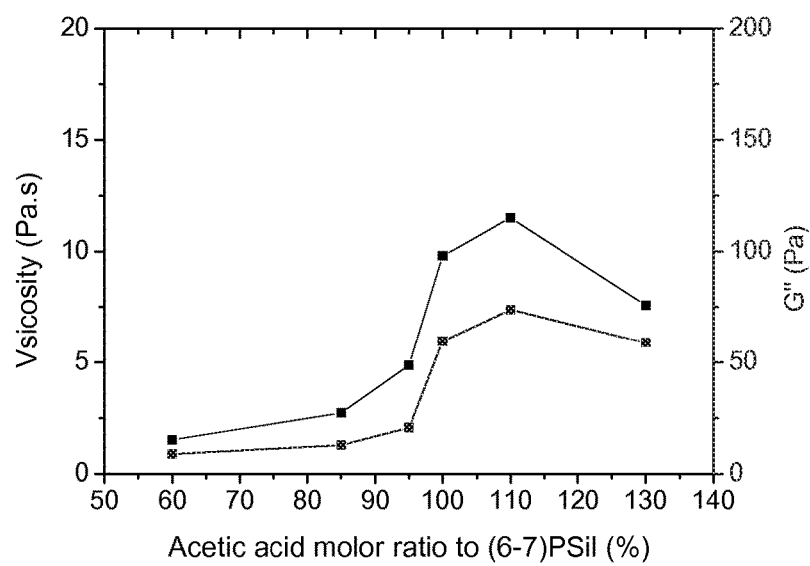
FIG. 30 depicts viscosity (top curve) and G" (bottom curve, at 1.2% strain and 1 Hz frequency) of PM1 as a function of different amounts of added acetic acid.

The viscosities and G" values of ammonium carboxylates with different mole ratios of benzoic acid and acetic acid to amino groups in 6-7PSil were also investigated (FIGS. 29 and 30). The magnitudes of both properties increased with increasing acid concentrations and reached maxima at ca. 110% molar ratios. The reason for the initial increases can be attributed to the creation of more electrostatic crosslinks (i.e., pairs of cations and anions on different chains becoming associated). The reason for the maximum occurring at greater than 1:1 molar ratios of acid to 6-7PSil is probably a consequence of both entropic and to electrostatic factors: as the fraction of amino groups of the 6-7PSil that are protonated is increased, the ability of the remaining amino groups to add a proton decreases due to electrostatic repulsion. Even at a slight excess of acid, where the maxima in viscosity and G" are observed, it is highly probable that some of the amino groups remain unprotonated; our analytical methods are not capable of detecting very small amounts of unprotonated amino groups. Addition of even more acid may disturb the ordering of inter-chain electrostatic interactions between protonated amino groups, leading to more fluid materials.

Figure 6:
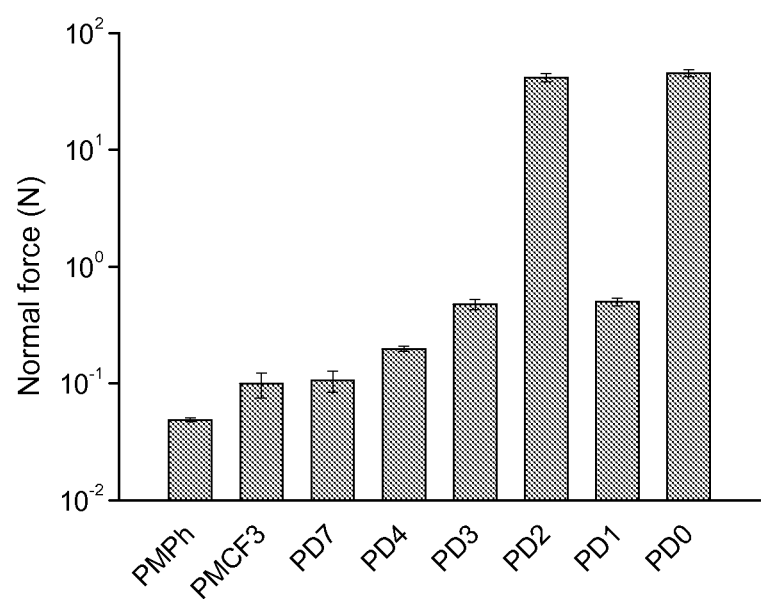
FIG. 6 tabulates maximum normal force measurements to break 6-7PSil ammonium carboxylate films between steel plates.
Figure 7:
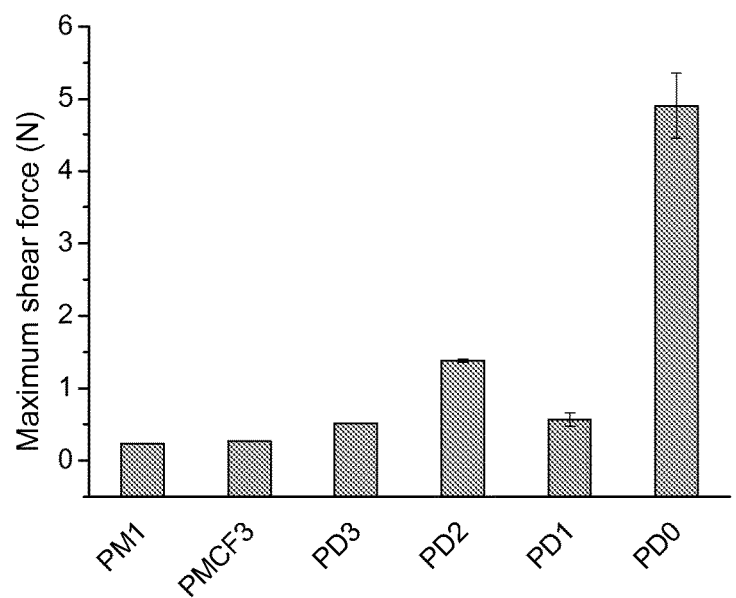
FIG. 7 depicts maximum shear force necessary to move films of 6-7PSil ammonium salts

The relative strengths of adhesion of films of some of the salts have been determined qualitatively by extensional rheology. The maximum force necessary to break the films was measured while increasing the gap between the steel plates of our rheometer. This force is a relative value, because it depends strongly on the rate of plate separation, the initial gap (i.e., film thickness), and plate area. In the experiments described, these factors have been maintained constant. The maximum normal forces of the ammonium carboxylates are much larger than that of 6-7PSil (~0.01 N) from which they were derived, and they correlate with the (absolute) values of the viscosities and moduli (FIG. 6). In addition, the relative shear force required to break films adhering to glass of some of the salts were measured using a universal testing machine (FIG. 7). The trend is similar to that found using extensional rheology.

Figure 8:
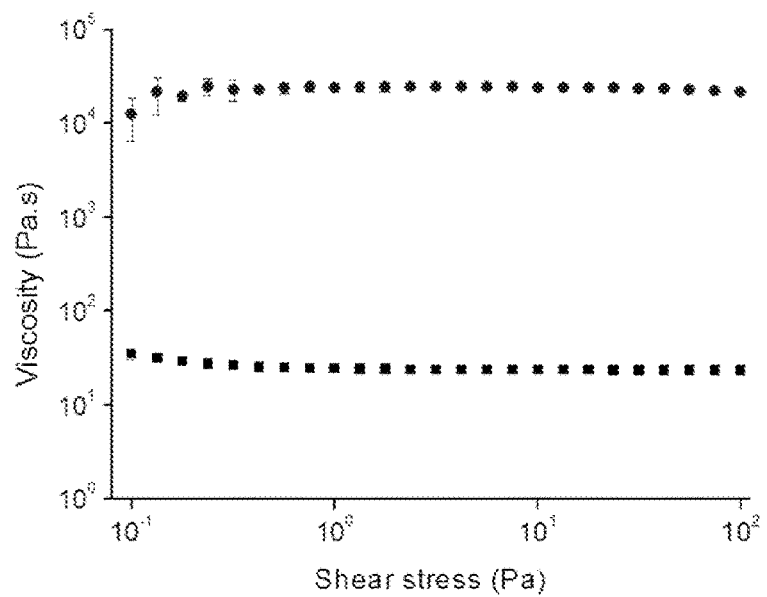
FIG. 8 depicts viscosity of 6-7PSil ammonium acrylate (PMAA) before (bottom curve) and after (upper curve) irradiation.
Figure 9:
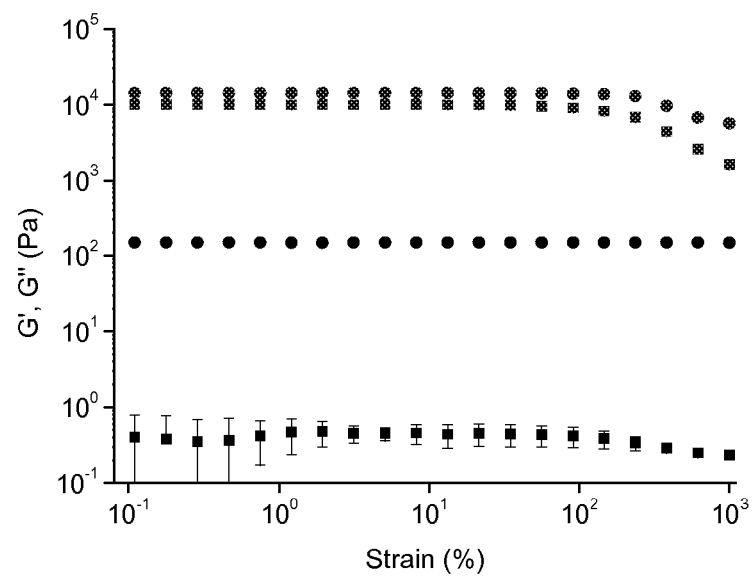
FIG. 9 depicts moduli (1 Hz frequency) of 6-7PSil ammonium acrylate (PMAA) before (lower two curves) and after (upper two curves) irradiation (G', square; G", circle).
Figure 10:
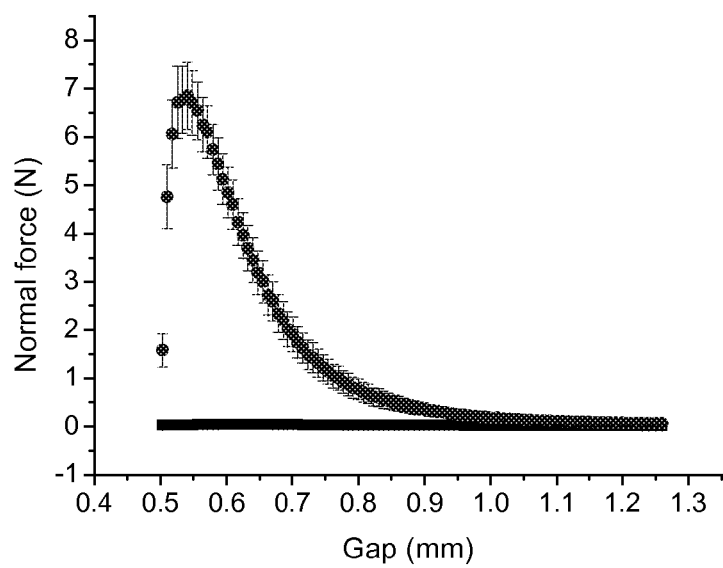
FIG. 10 depicts shear force versus extension of a 6-7PSil ammonium acrylate (PMAA) film between glass plates before (lower curve) and after (upper curve) irradiation.
Figure 31:
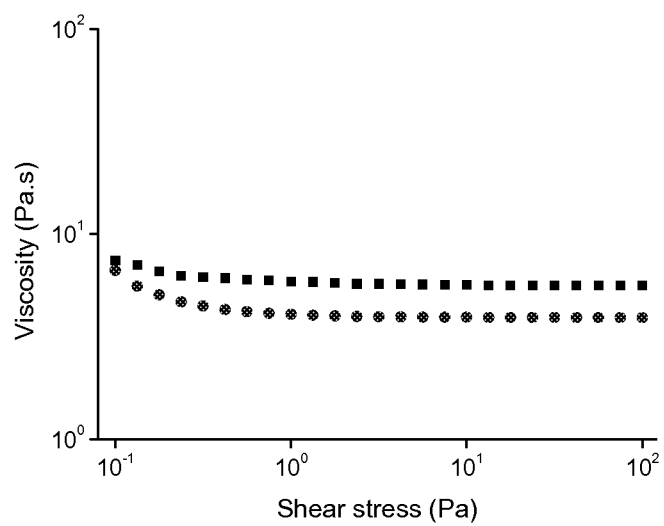
FIG. 31 depicts viscosity of PM2 with 3 wt % Darocur 1173 before (squares) and after (circles) irradiation.
Figure 32:
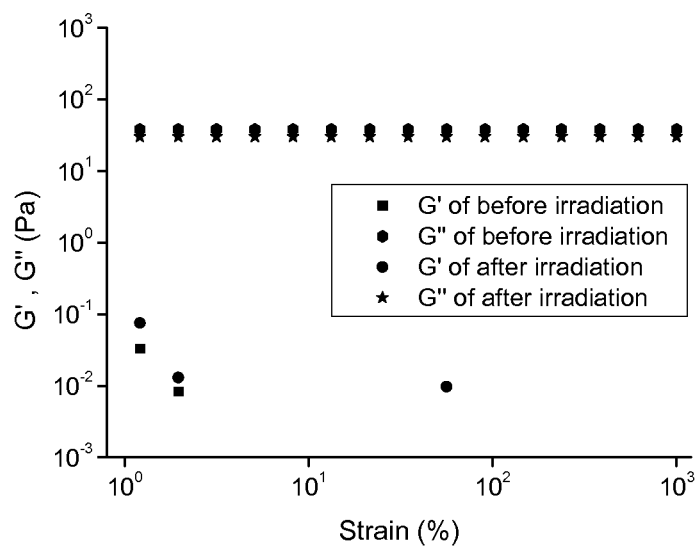
FIG. 32 depicts moduli of PM2 with 3 wt % Darocur 1173 (at 1 Hz frequency) before and after irradiation.
Figure 33:
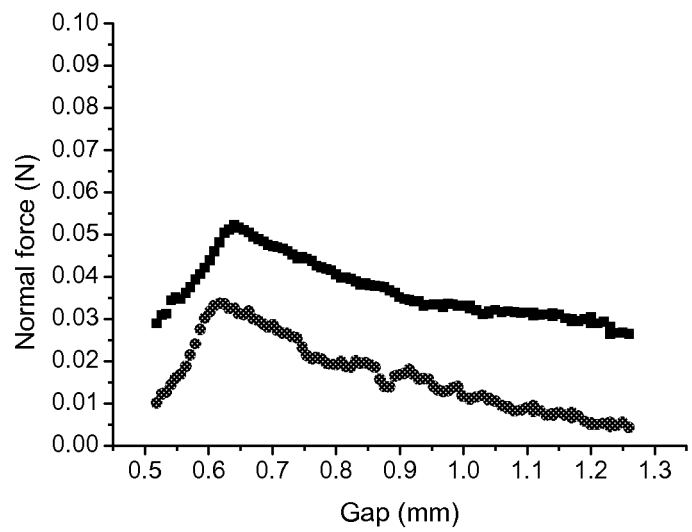
FIG. 33 depicts normal force from extensional rheology of PM2 with 3 wt % Darocur 1173 before (upper curve) and after (lower curve) irradiation.

Materials obtained from free radical-initiated polymerization of olefin-containing carboxylic acid monomers. Photo-initiated (by irradiation in the presence of added radical initiator such as Darocur 1173, which is 2-hydroxy-2-methyl-1-phenyl-propan-1-one), free-radical reaction of the 6-7PSil ammonium acrylate led to large increases in the viscosities (FIG. 8) and G' and G" values (FIG. 9), suggesting that the expected polyacrylate had been formed. In addition, the adhesion of the polymerized material increased significantly (FIG. 10): the normal force increased from 0.13 N before irradiation to 5.40 N after it. By comparison (and again, as expected), no increase in adhesion was found when a sample of 6-7PSil ammonium propionate was irradiated in the presence of the same concentration of 2-hydroxy-2-methyl-1-phenyl-propan-1-one (FIGS. 31-33).

By contrast, vinylbenzoic acid was polymerized when it was irradiated in 6-7PSil in the presence of the free-radical initiator. From FIG. 9, it can be seen that the viscosity, moduli and normal force of the ammoniumpolysiloxane vinylbenzoate increased markedly after irradiation. Although these changes were observed qualitatively as well when the ammoniumpolysiloxane acrylate was irradiated, a white solid, identified as poly(vinylbenzoic acid) (FIG. 10) was isolated when the irradiated sample was extracted as described in the Experimental Part. The material prepared by irradiation of ammoniumpolysiloxane vinylbenzoate constitutes an interpenetrating network.

Similarly, irradiation of the 6-7PSil/methacrylic acid system in the presence of initiator led to increases in the viscosity, moduli and normal force as a result of the formation of poly(methyl methacrylate) (that was isolated after the normal work-up procedure). Thus, the increases in the rheological properties upon irradiation of both PMMA and PMVPh can be attributed to establishment of interpenetrating networks as the monomers are polymerized.

Representative Syntheses. 6-7PSil glutarate (PD3) was synthesized by refluxing and stirring 3.00 g 6-7PSil, 0.169 g glutaric acid and 5.0 mL methylene chloride for 3 h in the air. The solvent was removed by placing it sequentially on a rotary evaporator under dynamic reduced pressure (150 mm Hg) for >24 h at room temperature, and then under dynamic reduced pressure of 0.5 mm Hg for 3 h at 40-50° C.

IR: 2964, 2905 cm$^{-1}$ (C—H), 1563 cm$^{-1}$ (C=O)

$^1$H NMR: 6.58-7.88 ppm (br, 6H, $^+$NH$_3$), 2.84 ppm (m, 4H, NCH$_2$), 2.18 ppm (t, 4H, CH$_2$COO$^-$), 1.83 ppm (m, 2H, CH$_2$CCOO$^-$), 1.73 ppm (m, 4H, $^+$NCCH$_2$), 0.54 ppm (t, 4H, $^+$NCCCH$_2$)

6-7PSil ammonium acrylate (PMAA) was synthesized by stirring 3.00 g 6-7PSil and 0.184 g acrylic acid at room temperature for 1 h in air. Methylene chloride (5.0 mL) was added and the mixture was refluxed and stirred for 3 h. The solvent was removed by placing it sequentially on a rotary evaporator under dynamic reduced pressure (150 mm Hg) for >24 h at room temperature, and then under dynamic reduced pressure of 0.5 mm Hg for 3 h at 40-50° C.

IR: 2963, 2905 cm$^{-1}$ (C—H), 1635 cm$^{-1}$ (C=O), 1565 cm$^{-1}$ (C=O)

$^1$H NMR: 6.70-7.65 ppm (br, 3H, $^+$NH$_3$), 6.09 ppm (m, 2H, =CH$_2$), 5.52 ppm (t, 1H, =CH), 2.79 ppm (m, 2H, $^+$NCH$_2$), 1.65 ppm (m, 4H, $^+$NCCH$_2$), 0.52 ppm (t, 4H, $^+$NCCCH$_2$)

D$_2$EDA ammonium acetate was synthesized by stirring 3.00 g D$_2$EDA and 0.798 g acetic acid at room temperature for 1 h. Then, the mixture was refluxed and stirred for 3 h in air after adding 5.0 mL methylene chloride. The solvent was removed by placing it sequentially on a rotary evaporator, under dynamic reduced pressure (150 mm Hg) for >24 h at room temperature and under dynamic reduced pressure of 0.5 mm Hg for 3 h at 40-50° C.

IR: 2962, 2868 cm$^{-1}$ (C—H), 1565 cm$^{-1}$ (C=O)

$^1$H NMR: 5.41-5.88 ppm (br, 5H, $^+$NH$_3$, $^+$NH$_2$), 3.39 ppm (t, 4H, $^+$NCCH$_2$N$^+$), 3.22 ppm (t, 2H, $^+$NCH$_2$CC), 1.65 ppm (m, 2H, $^+$NCCH$_2$), 0.46 ppm (t, 2H, $^+$NCCCH$_2$)

Example 2

6-7PSil Vinylbenzoate and Product of Irradiation

Figure 34:
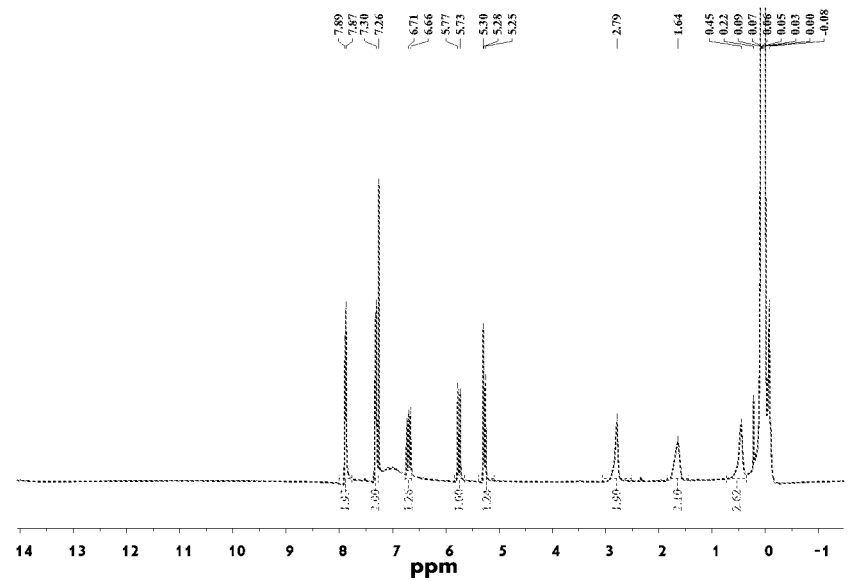
FIG. 34 depicts the $^1$H NMR spectrum of 6-7PSil vinylbenzoate in CDCl$_3$.

To further study the reaction of polysiloxane ammonium salts with acids containing poylmerizable olefins upon radiation, 6-7PSil vinylbenzoate was synthesized using vinylbenzoic acid with the same procedure with benzoic acid reported above. The $^1$H NMR spectrum of this product is shown in FIG. 34, in which it can be seen that the ammonium salt was synthesized successfully: four hydrogens at 7.89 and 7.32 are from benzene ring, broad peak from 7.10 to 6.77 ppm is from ammonium salt, three hydrogens at 6.71, 5.77 and 5.30 ppm are from double bond, and six hydrogens at 2.79, 1.64 and 0.45 are from propyl attached to nitrogen.

Figure 35:
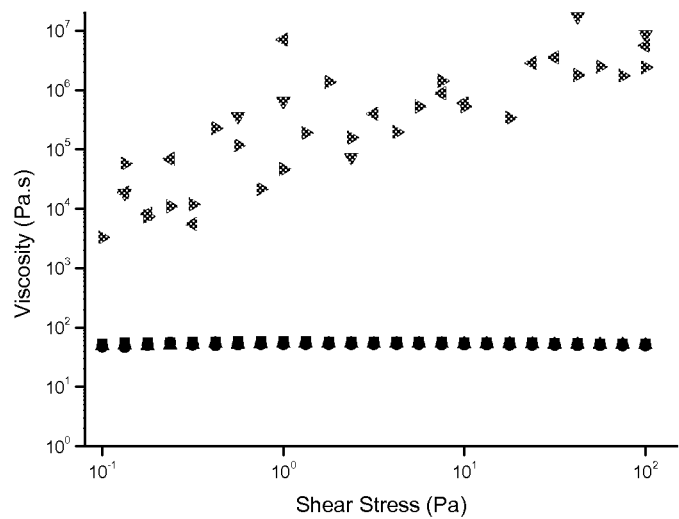
FIG. 35 depicts viscosity of 6-7Psil vinylbenzoate before (bottom) and after (top) irradiation with 3 wt % Darocur 1173 as photoinitiator.
Figure 36:
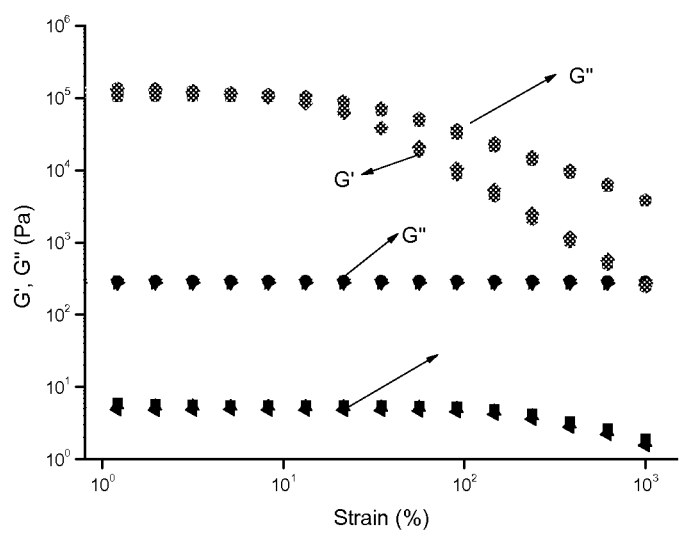
FIG. 36 depicts moduli of 6-7PSil methacrylate before (bottom curves) and after (top curves) irradiation with 3 wt % Darocur 1173 as photoinitiator at 1 Hz frequency.

From the rheology results it can be seen that the viscosity and moduli increased after irradiation (FIG. 35 and FIG. 36), which is similar to vinylbenzoate and methacrylate systems.

Figure 37:
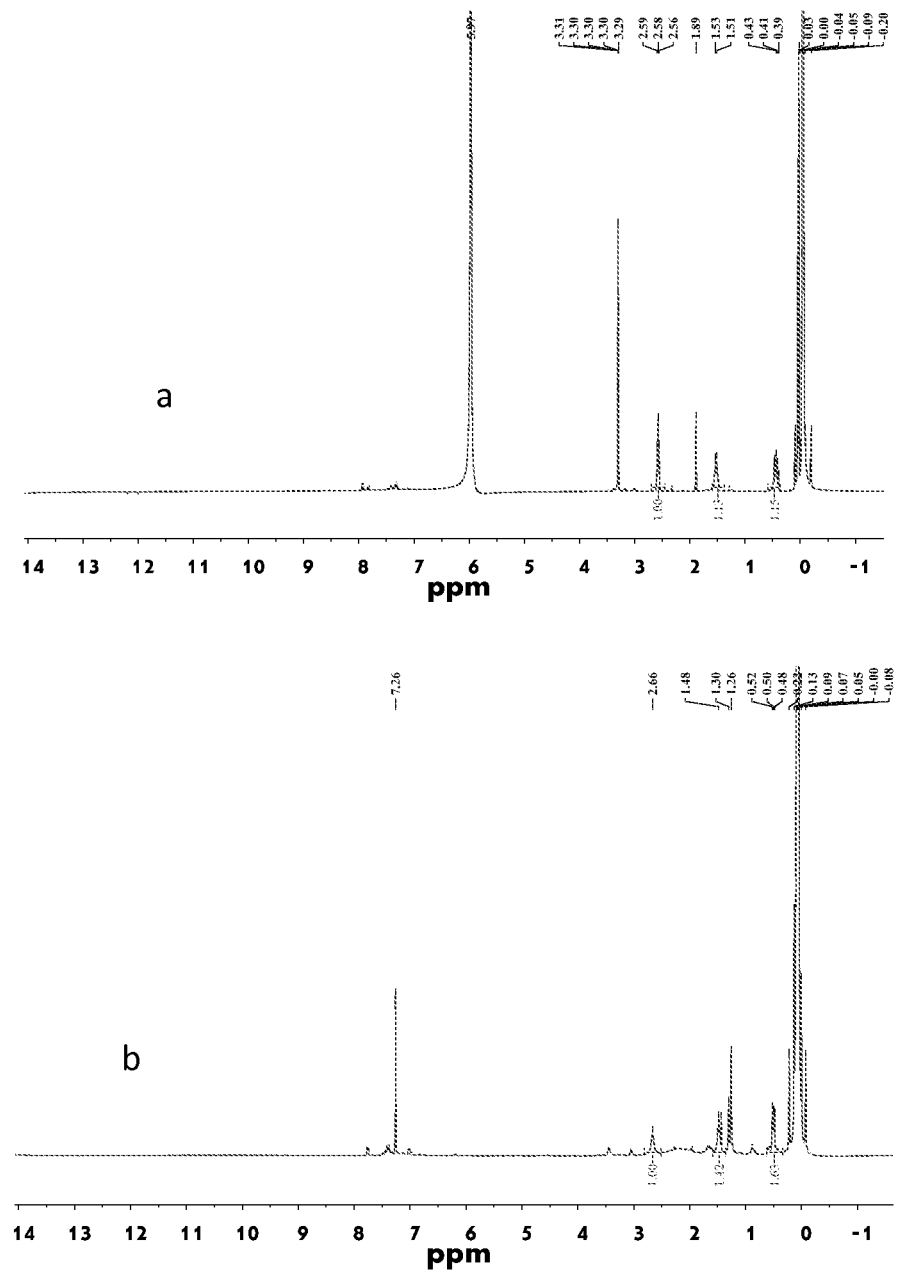
FIG. 37 depicts $^1$H NMR spectra of hydrolysis product in CD$_3$OD (a), first extraction product (b), second extraction product (c) in CDCl$_3$, liquid residue after extraction in D$_2$O (d) and solid residue after extraction in CD$_3$OD (e) of 6-7PSil vinylbenzoate with 3 wt % Darocur 1173 as photoinitiator after irradiation.
Figure 37:
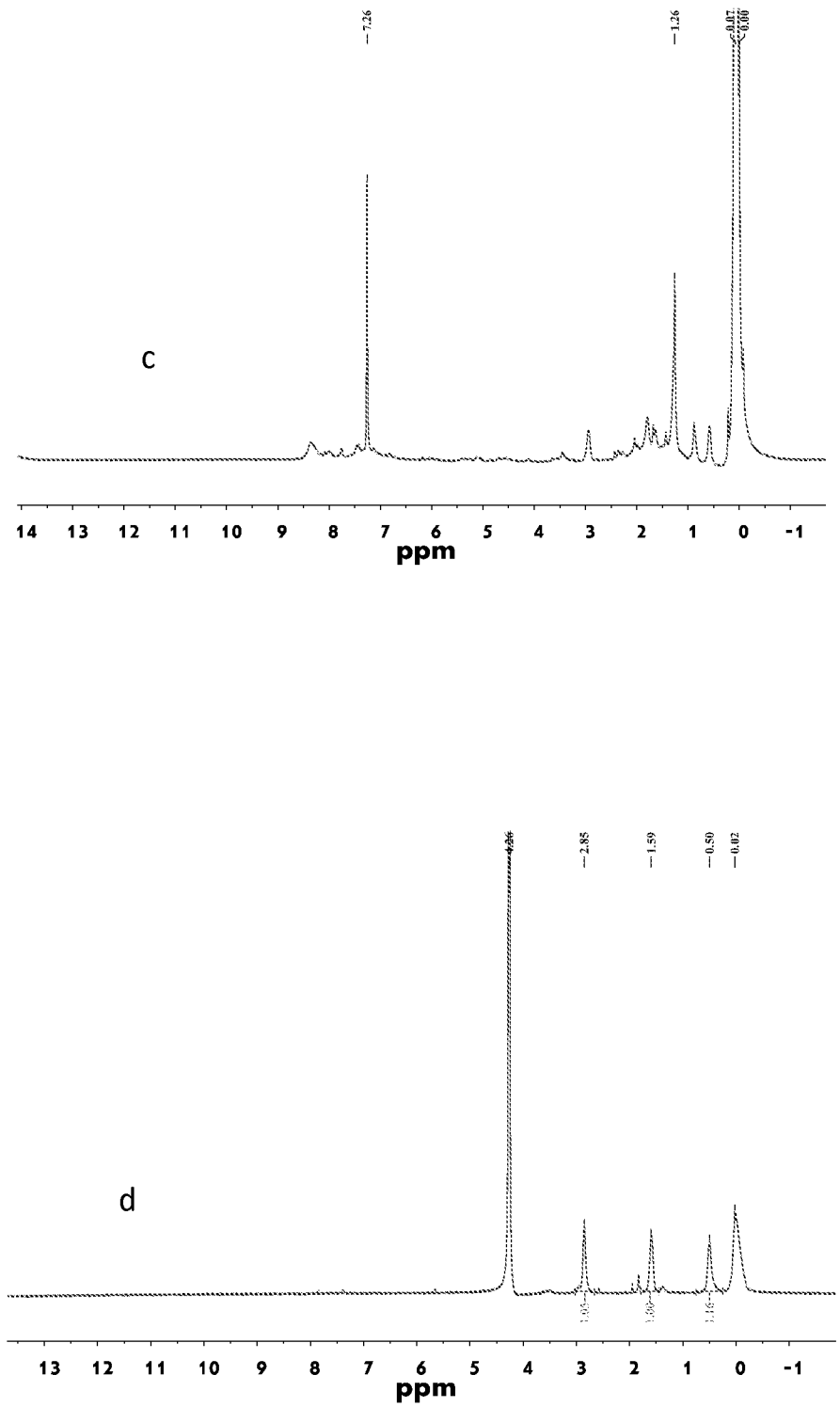
Figure 37:
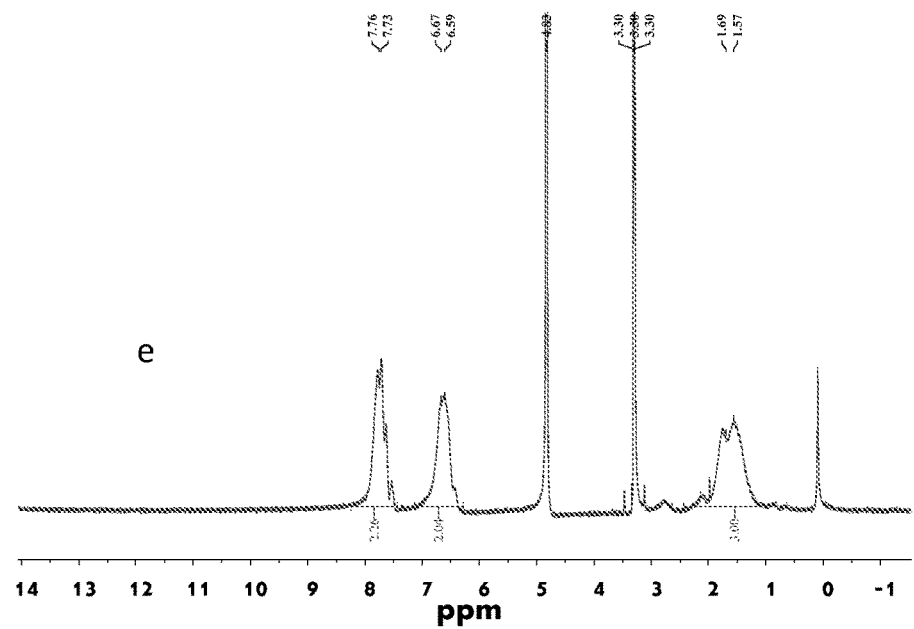

Then hydrolysis of this ammonium salt was performed with the same procedure as the methacrylate system. The crude product was mixed with 40 mL 0.25 M NaOH aqueous solution and allowed to stir for 3 h at 65° C. After vacuum filtration, the liquid was dried completely to obtain a crude hydrolysis product. During the extraction a white solid precipitated. After the extraction was complete, the solid precipitate was separated and dried. The $^1$H NMR spectra of the products obtained from hydrolysis process are shown in FIG. 37. It can be seen from the spectrum of solid residue after extraction (FIG. 37(e)) that there are three broad peaks at 7.76, 6.67 and 1.69 ppm with integration ratio of approximately 2:2:3, which can assigned to the four hydrogens on the benzene ring and the three hydrogens of the carbon chain of polyvinylbenzoic acid.

Figure 38:
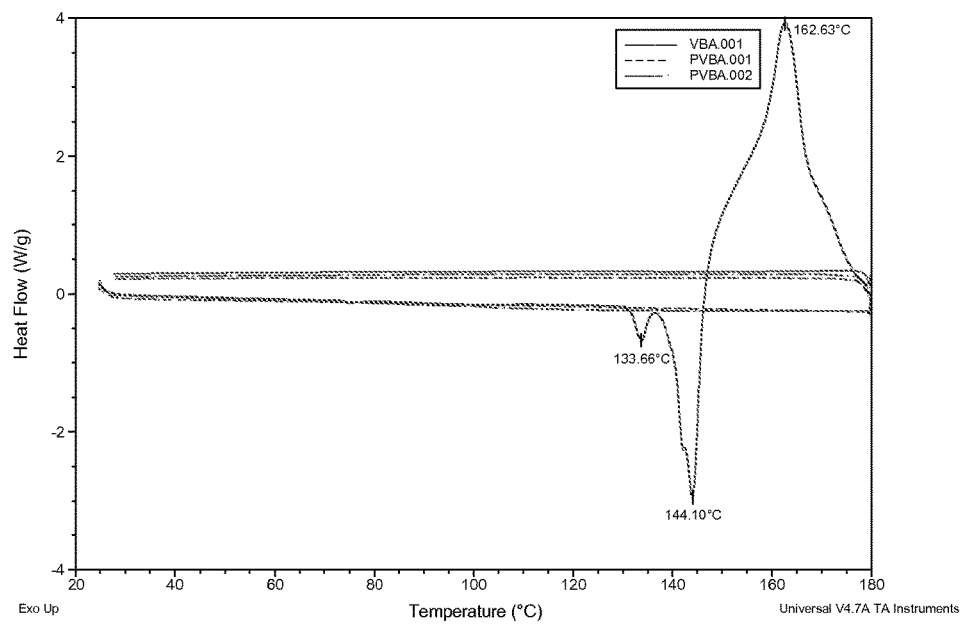
FIG. 38 depicts DSC diagrams of vinylbenzoic acid (solid) and polyvinylbenzoic acid (dot for first run and dash for second run) obtained from solution polymerization.

To further confirm the structure of the solid residue after extraction obtained from hydrolysis of irradiated 6-7PSil vinylbenzoate, a sample of polyvinylbenzoic acid was prepared through free radical solution polymerization. The process is dissolving 600 mg vinylbenzoic acid and 2 wt % AIBN in 10 g dioxane, and bubbling nitrogen through solution for 0.5 h, then stirring the solution for 3 h at 85-90° C. After cooling the solution to room temperature, it was poured into 200 mL hexane to obtain a yellow solid followed by washing with chloroform three times. Finally, the product was dried in a vacuum oven at 50° C. overnight. From the DSC results shown in FIG. 38, vinylbenzoic acid showed two peaks at 134 and 144° C., which correspond to its melting point 142-144° C. The product obtained after the polymerization in solution show nothing in this area, which means that there is no monomer left. Its $^1$H NMR spectrum was identical to that shown in FIG. 37(e). These results confirm that the solid residue is polyvinylbenzoic acid.

Example 3

6-7PSil Methacrylate and D$_2$EDA Acrylate

Figure 39:
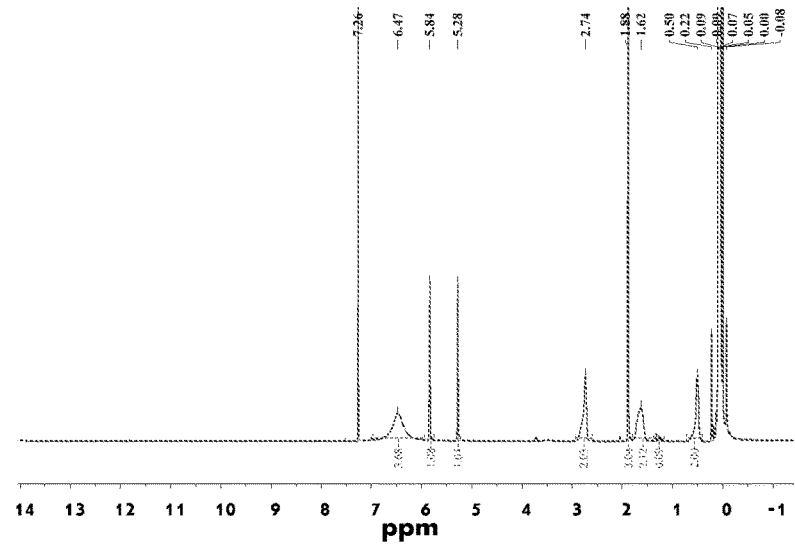
FIG. 39 depicts the $^1$H NMR spectrum of 6-7Psil methacrylate in CDCl$_3$.
Figure 40:
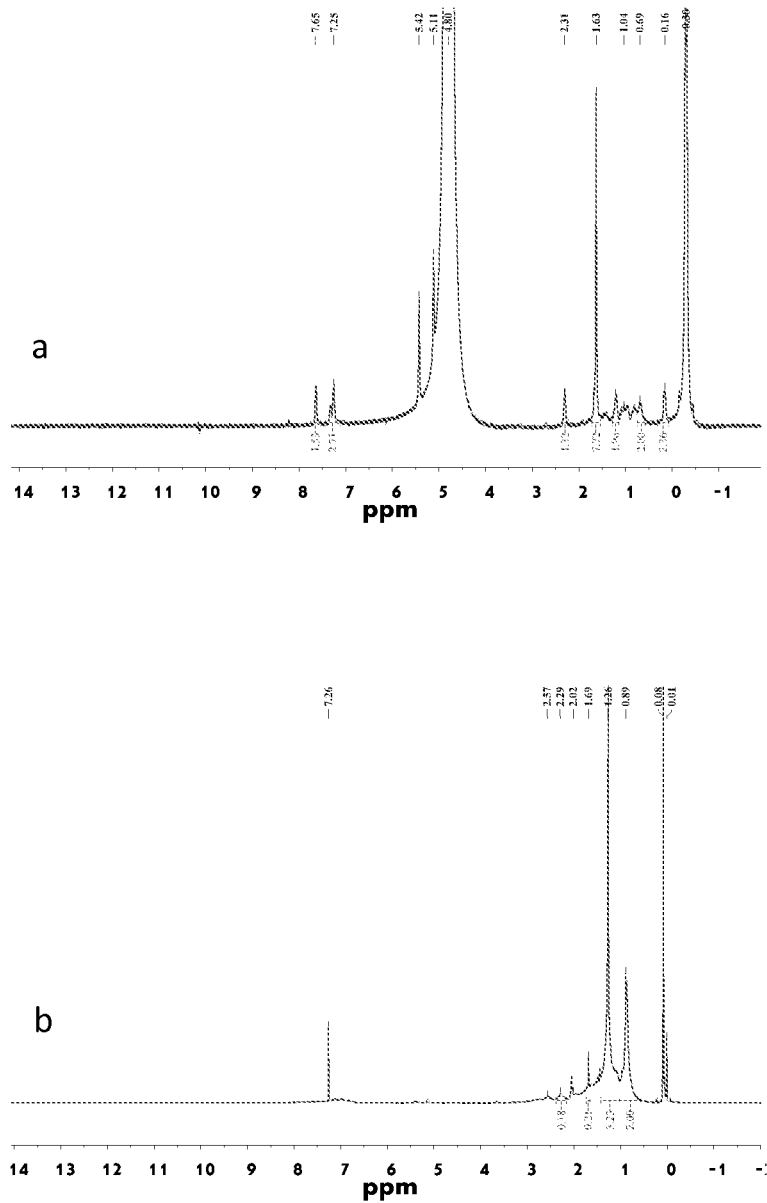
FIG. 40 depicts $^1$H NMR spectra of crude hydrolysis product in D$_2$O (a), first extraction product (b), and second extraction product (c) in CDCl$_3$.
Figure 40:
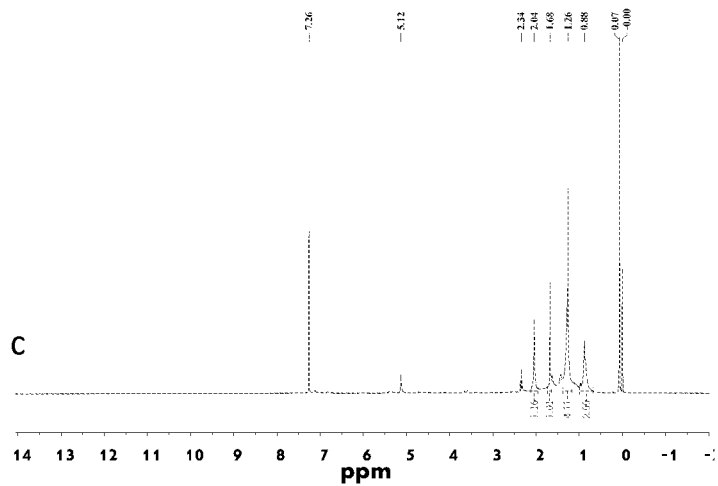

The 6-7PSil methacrylate was synthesized and investigated, and it was noted that the viscosity and moduli of 6-7PSil methacrylate increased greatly after irradiation. A hydrolysis similar to that in Example 2 was undertaken of the product after irradiation. The crude product (400 mg) was mixed with 40 mL 0.25 M NaOH aqueous solution and allowed to stir for 3 h at 65° C. After vacuum filtration, one half of the liquid was dried completely to obtain a crude hydrolysis product. Other half part of this liquid was extracted with 3×50 mL ether, methylene chloride and ethyl acetate separately, then the organic layers were combined and dried with anhydrous Na$_2$SO$_4$ overnight, then the solvent evaporated and the residue dried in a vacuum oven at 50° C. overnight; the resulting product is termed herein the first extraction product. The water phase obtained in the first extraction was neutralized with 1 M HCl in an ice bath to pH 3 then extracted with same procedure as above to obtain a product termed herein the second extraction product. For reference, the $^1$H NMR spectrum of 6-7PSil methacrylate in CDCl$_3$ is shown in FIG. 39. In this spectrum, the three proton signals at 6.47 ppm correspond to the ammonium salt, the two protons at 5.84 and 5.28 ppm are assigned to the hydrogen attached to the double bond, the three protons at 2.74, 1.62 and 0.50 ppm are assigned to the propyl group attached to the nitrogen, and the three protons at 1.88 ppm are assigned to the methyl group of methacrylic acid. The spectrum of the hydrolysis product (FIG. 40(a)) reveals the presence of methacrylic acid due to the signals at 5.42 and 5.11 ppm for the double bond protons and 1.63 ppm for the methyl group. There does not appear to be any polymethacrylic acid present. For the first (FIG. 40(b)) and second (FIG. 40(c)) extraction products, polymethacrylic acid appears to be present because of peaks at 1.26 and 0.89 ppm, corresponding to methylene and methyl protons.

Figure 41:
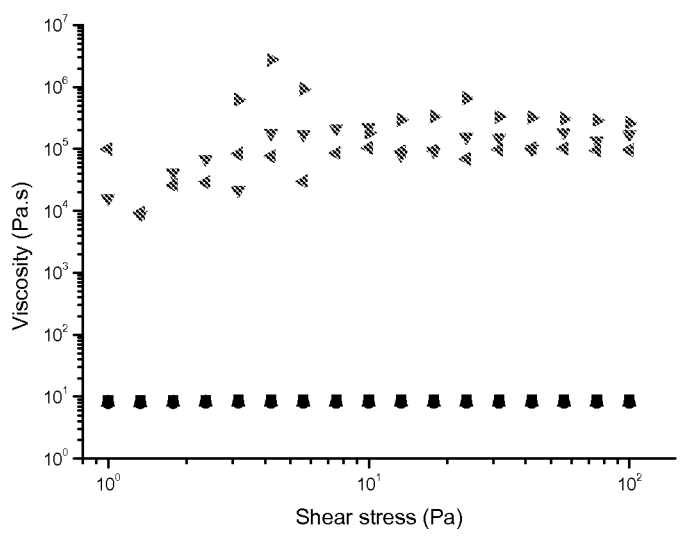
FIG. 41 depicts viscosity of 6-7Psil methacrylate before (bottom curve) and after (upper curve) irradiation with 3 wt % Darocur 1173 as photoinitiator.
Figure 42:
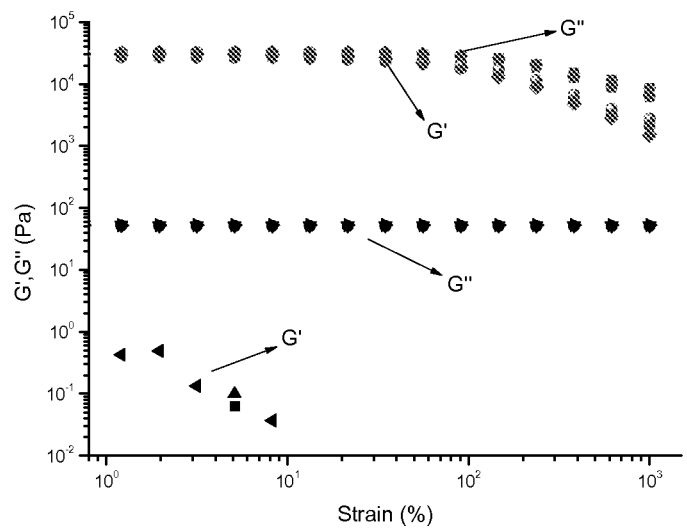
FIG. 42 depicts moduli of 6-7PSil methacrylate before (bottom curve) and after (upper curve) irradiation with 3 wt % Darocur 1173 as photoinitiator.
Figure 43:
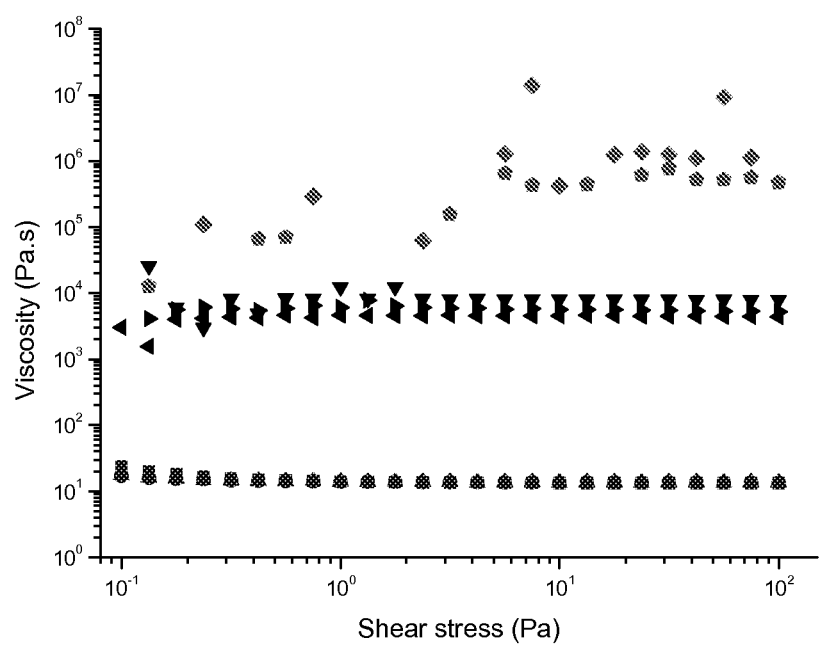
FIG. 43 depicts the viscosity of D$_2$EDA (bottom curve) and D$_2$EDA acrylate before (middle curve) and after (upper curve) irradiation with 3 wt % Darocur 1173 as photoinitiator.
Figure 44:
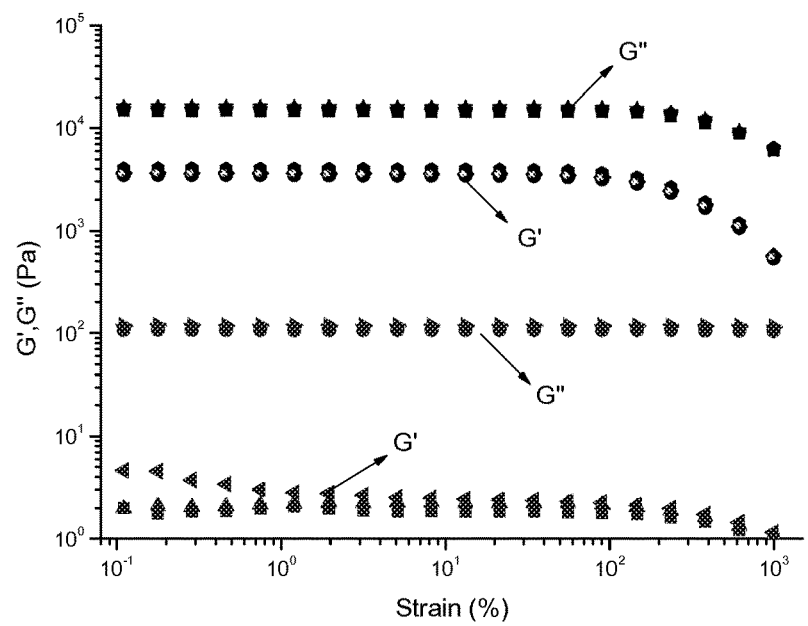
FIG. 44 depicts moduli of D$_2$EDA (bottom curve) and D$_2$EDA acrylate (upper curve).
Figure 45:
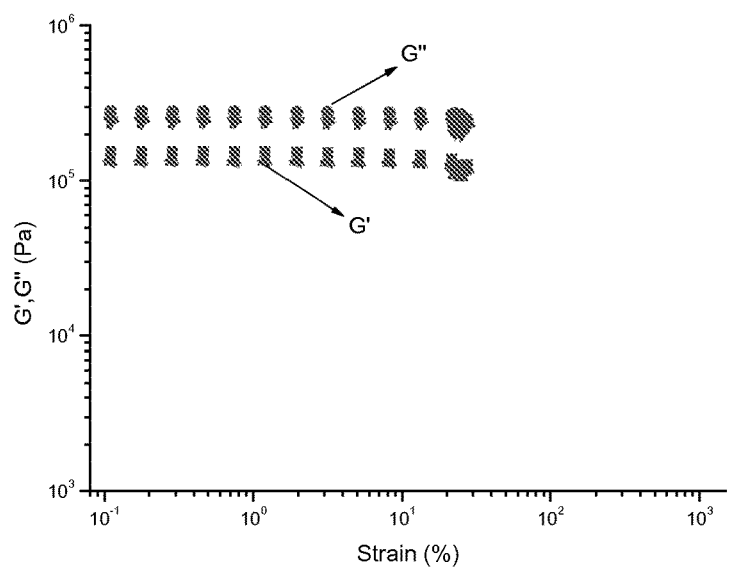
FIG. 45 depicts moduli D$_2$EDA acrylate after irradiation with 3 wt % Darocur 1173 as photoinitiator.
Figure 46:
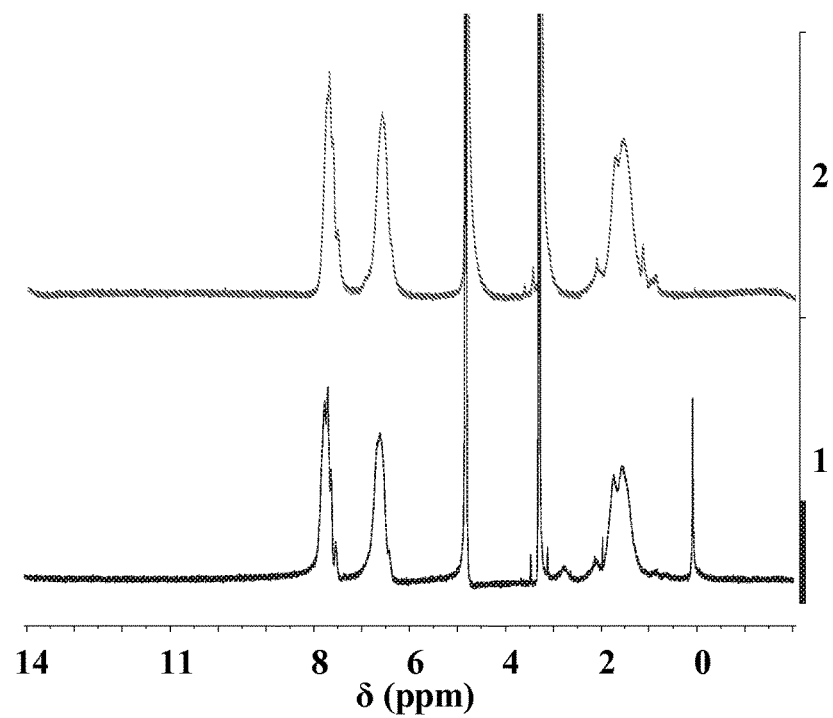
FIG. 46 depicts vertically offset $^1$H NMR spectra in CD$_3$OD of the hydrolysis product of ammoniumpolysiloxane vinylbenzoate after irradiation (1), and polyvinylbonzoic acid obtained from free radical solution polymerization (2).

The viscosity and moduli of 6-7PSil methacrylate increased after irradiation (FIG. 41 and FIG. 42), similar to the corresponding acrylate. Also investigated were the viscosity and moduli for D$_2$EDA acrylate before and after irradiation (FIG. 43-FIG. 45). This yielded similar results to 6-7PSil acrylate. The viscosity and moduli of D$_2$EDA acrylate were higher than that of D$_2$EDA, and increased further after irradiation.

EQUIVALENTS

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

We claim:

1. A composition comprising a polymer composition consisting of a polysiloxane comprising a plurality of pendant primary, secondary, or primary and secondary amines; and a plurality of in situ photopolymerized olefin-containing carboxylic acids, wherein:
    each of the pendant amines is attached to the polysiloxane via a C$_1$-C$_6$ alkyl group optionally substituted with one or more alkyl, haloalkyl, halide, aryl, or aralkyl groups;
    the pendant amines do not comprise diamines; and
    the polysiloxane and the plurality of in situ photopolymerized olefin-containing carboxylic acids form a three-dimensional interpenetrating network mediated by electrostatic interactions.

2. The composition of claim 1, wherein the olefin-containing carboxylic acids are selected from the group consisting of acrylic acid, methacrylic acid, and vinylbenzoic acid.

3. The composition of claim 1, wherein the pendant amines comprise primary amines.

4. The composition of claim 1, wherein the pendant amines comprise secondary amines.

5. A composition for controlled release of a compound, comprising the composition of claim 1; and the compound.

6. The composition of claim 1, wherein the pendant amines comprise primary amines and secondary amines.

7. A battery, comprising the composition of claim 1.

* * * * *